US010099020B2

(12) United States Patent
Davidson et al.

(10) Patent No.: US 10,099,020 B2
(45) Date of Patent: Oct. 16, 2018

(54) DRUG DOSE CARTRIDGE FOR AN INHALER DEVICE

(71) Applicant: Syqe Medical Ltd., Tel-Aviv (IL)

(72) Inventors: Perry Davidson, Tel-Aviv (IL); Aaron Schorr, Bat-Yam (IL); Binyamin Schwartz, Sde Eliezer (IL); Roee Lifshitz, Moshav Beit Hillel (IL)

(73) Assignee: Syqe Medical Ltd., Tel-Aviv (IL)

( * ) Notice: Subject to any disclaimer, the term of this patent is extended or adjusted under 35 U.S.C. 154(b) by 0 days.

(21) Appl. No.: 15/308,370

(22) PCT Filed: Jun. 30, 2015

(86) PCT No.: PCT/IL2015/050677
§ 371 (c)(1),
(2) Date: Nov. 2, 2016

(87) PCT Pub. No.: WO2016/001925
PCT Pub. Date: Jan. 7, 2016

(65) Prior Publication Data
US 2017/0095624 A1  Apr. 6, 2017

Related U.S. Application Data

(60) Provisional application No. 62/164,710, filed on May 21, 2015, provisional application No. 62/086,208, (Continued)

(51) Int. Cl.
*A61M 15/00* (2006.01)
*A24F 47/00* (2006.01)
(Continued)

(52) U.S. Cl.
CPC ......... *A61M 15/002* (2014.02); *A24F 47/008* (2013.01); *A61K 9/007* (2013.01);
(Continued)

(58) Field of Classification Search
CPC ............... A61M 11/042; A61M 15/00; A61M 15/0003; A61M 15/0028; A61M 15/0043;
(Continued)

(56) References Cited

U.S. PATENT DOCUMENTS 3,203,432 A    8/1965  Green et al.
3,894,544 A    7/1975  Egri
(Continued)

FOREIGN PATENT DOCUMENTS

AU    199641966    5/1996
EP       1358902   11/2003
(Continued)

OTHER PUBLICATIONS

Communication Relating to the Results of the Partial International Search dated May 18, 2012 From the International Searching Authority Re. Application No. PCT/IL2011/050071.
(Continued)

*Primary Examiner* — Kathryn E Ditmer

(57) ABSTRACT

Devices and methods are described for preparing, managing, and/or administering metered doses of substances for vaporized administration. In some embodiments, dose cartridges comprising at least one botanical substance include a heating element integrated into the cartridge in close contact with the botanical substance. In some embodiments, cartridge-mounted doses are stored in a magazine, optionally in carousel form, before use. Transport of a cartridge from a magazine to an electrically operated vaporizing chamber which activates the heating element is provided by a mechanical pickup means.

25 Claims, 15 Drawing Sheets

Related U.S. Application Data filed on Dec. 2, 2014, provisional application No. 62/085,772, filed on Dec. 1, 2014, provisional application No. 62/035,588, filed on Aug. 11, 2014, provisional application No. 62/019,225, filed on Jun. 30, 2014.

(51) Int. Cl.

| | | |
|---|---|---|
| *A61M 16/20* | (2006.01) | |
| *A61K 9/00* | (2006.01) | |
| *A61K 36/185* | (2006.01) | |
| *H05B 1/02* | (2006.01) | |
| *A61K 31/352* | (2006.01) | |
| *A61M 11/04* | (2006.01) | |

(52) U.S. Cl.
CPC .......... *A61K 9/0073* (2013.01); *A61K 31/352* (2013.01); *A61K 36/185* (2013.01); *A61M 11/042* (2014.02); *A61M 15/0028* (2013.01); *A61M 15/0045* (2013.01); *A61M 15/0065* (2013.01); *A61M 16/20* (2013.01); *H05B 1/025* (2013.01); *A61M 11/041* (2013.01); *A61M 15/005* (2014.02); *A61M 2205/3334* (2013.01); *A61M 2205/3368* (2013.01); *A61M 2205/36* (2013.01)

(58) Field of Classification Search
CPC ........... A61M 15/0045; A61M 15/0046; A24F 47/002; A24F 47/004; A24F 47/008; H05B 1/025; A61K 9/007
See application file for complete search history.

(56) References Cited

U.S. PATENT DOCUMENTS

| | | | |
|---|---|---|---|
| 4,735,358 A | 4/1988 | Morita et al. | |
| 4,966,171 A | 10/1990 | Serrano et al. | |
| 4,969,477 A | 11/1990 | Yagisawa | |
| 5,301,666 A | 4/1994 | Lerk et al. | |
| 5,404,871 A | 5/1994 | Goodman et al. | |
| 5,333,106 A | 7/1994 | Lanpher et al. | |
| 5,388,594 A | 2/1995 | Counts et al. | |
| 5,479,948 A | 1/1996 | Counts et al. | |
| 5,649,554 A | 7/1997 | Sprinkel et al. | |
| 5,655,520 A | 8/1997 | Howe et al. | |
| 5,792,057 A | 8/1998 | Rubsamen et al. | |
| 6,703,418 B2 | 3/2004 | Plasse | |
| 6,761,164 B2 | 7/2004 | Amirpour et al. | |
| 7,088,914 B2 | 8/2006 | Whittle et al. | |
| 7,169,378 B2 | 1/2007 | Rabinowitz et al. | |
| 7,287,530 B1 | 10/2007 | Stuart | |
| 7,537,005 B2 | 5/2009 | Dave | |
| 7,987,846 B2 | 8/2011 | Hale et al. | |
| 8,235,037 B2 | 8/2012 | Hale et al. | |
| 8,408,200 B2 | 4/2013 | Clark et al. | |
| 8,615,407 B2 | 12/2013 | Hyde et al. | |
| 2001/0027789 A1 | 10/2001 | Goede et al. | |
| 2002/0168322 A1 | 11/2002 | Clark et al. | |
| 2003/0037785 A1 | 2/2003 | Sonntag | |
| 2003/0041859 A1 | 3/2003 | Abrams et al. | |
| 2003/0062042 A1 | 4/2003 | Wensley et al. | |
| 2003/0168057 A1 | 9/2003 | Snyder et al. | |
| 2003/0200964 A1 | 10/2003 | Blakley et al. | |
| 2004/0045567 A1 | 3/2004 | Lewis et al. | |
| 2004/0069798 A1 | 4/2004 | Grey et al. | |
| 2004/0084044 A1 | 5/2004 | Childers et al. | |
| 2004/0099266 A1 | 5/2004 | Cross et al. | |
| 2004/0192760 A1 | 9/2004 | Whittle et al. | |
| 2005/0063686 A1 | 3/2005 | Whittle et al. | |
| 2005/0126562 A1 | 6/2005 | Rabinowitz et al. | |
| 2005/0244521 A1 | 11/2005 | Strickland et al. | |
| 2005/0268909 A1 | 12/2005 | Bonney et al. | |
| 2005/0268911 A1 | 12/2005 | Cross et al. | |
| 2006/0102175 A1 | 5/2006 | Nelson | |
| 2006/0120962 A1 | 6/2006 | Rabinowitz et al. | |
| 2006/0157491 A1 | 7/2006 | Whittle et al. | |
| 2006/0167084 A1 | 7/2006 | Dudley | |
| 2006/0258738 A1 | 11/2006 | Dieterich | |
| 2007/0072938 A1 | 3/2007 | Rose | |
| 2007/0122353 A1 | 3/2007 | Hale et al. | |
| 2007/0074721 A1 | 4/2007 | Harmer et al. | |
| 2007/0102013 A1 | 5/2007 | Adams et al. | |
| 2007/0209661 A1 | 9/2007 | Smyth et al. | |
| 2007/0240712 A1 | 10/2007 | Fleming et al. | |
| 2007/0286816 A1 | 12/2007 | Hale et al. | |
| 2008/0072898 A1 | 3/2008 | Quoniam | |
| 2008/0078382 A1 | 4/2008 | LeMahieu et al. | |
| 2008/0140250 A1 | 6/2008 | Dave | |
| 2008/0176885 A1 | 7/2008 | Holtman et al. | |
| 2008/0181942 A1 | 7/2008 | Zajicek | |
| 2008/0299048 A1 | 12/2008 | Hale et al. | |
| 2008/0311176 A1 | 12/2008 | Hale et al. | |
| 2009/0084865 A1 | 4/2009 | Maharajh | |
| 2009/0151722 A1 | 6/2009 | Eason et al. | |
| 2009/0197941 A1 | 8/2009 | Guy et al. | |
| 2009/0241949 A1 | 10/2009 | Smutney et al. | |
| 2009/0293888 A1 | 12/2009 | Williams et al. | |
| 2009/0308390 A1 | 12/2009 | Smutney et al. | |
| 2009/0320836 A1 | 12/2009 | Baker, Jr. | |
| 2010/0012118 A1 | 1/2010 | Storz | |
| 2010/0035978 A1 | 2/2010 | Guy et al. | |
| 2010/0154795 A1 | 6/2010 | Pentafragas | |
| 2010/0168228 A1 | 7/2010 | Bose | |
| 2010/0181387 A1 | 7/2010 | Zaffaroni et al. | |
| 2010/0204602 A1 | 8/2010 | Addington et al. | |
| 2010/0250280 A1 | 9/2010 | Sutherland | |
| 2010/0294278 A1 | 11/2010 | Mosier et al. | |
| 2010/0326438 A1 | 12/2010 | Dunne | |
| 2011/0030706 A1 | 2/2011 | Gibson et al. | |
| 2011/0036346 A1 | 2/2011 | Cohen et al. | |
| 2011/0038958 A1 | 2/2011 | Kikuchi et al. | |
| 2011/0126831 A1 | 6/2011 | Fernandez Pernia | |
| 2011/0244020 A1 | 10/2011 | Hale et al. | |
| 2011/0265806 A1 | 11/2011 | Alarcon et al. | |
| 2012/0252885 A1 | 10/2012 | Barbato | |
| 2012/0255546 A1 | 10/2012 | Goetz et al. | |
| 2012/0304990 A1 | 12/2012 | Todd | |
| 2012/0325227 A1 | 12/2012 | Robinson et al. | |
| 2013/0032139 A1 | 2/2013 | Hale et al. | |
| 2013/0081623 A1 | 4/2013 | Buchberger | |
| 2013/0087144 A1* | 4/2013 | Todd ................... | A61B 5/1171 128/203.14 |
| 2013/0112197 A1 | 5/2013 | Kruener et al. | |
| 2013/0213397 A1 | 8/2013 | Curtis et al. | |
| 2013/0276799 A1 | 10/2013 | Davidson et al. | |
| 2013/0333700 A1 | 12/2013 | Buchberger | |
| 2014/0060525 A1 | 3/2014 | Hale et al. | |
| 2014/0088045 A1 | 3/2014 | Rigas et al. | |
| 2014/0100249 A1 | 4/2014 | Sears et al. | |
| 2014/0144429 A1 | 5/2014 | Wensley et al. | |
| 2014/0190496 A1 | 7/2014 | Wensley et al. | |
| 2014/0238423 A1 | 8/2014 | Tucker et al. | |
| 2015/0064672 A1 | 3/2015 | Bars | |
| 2015/0075521 A1 | 3/2015 | Lee et al. | |
| 2015/0090253 A1 | 4/2015 | Farrow | |
| 2015/0122252 A1 | 5/2015 | Frija | |
| 2015/0136124 A1 | 5/2015 | Aronie et al. | |
| 2015/0237913 A1* | 8/2015 | Suzuki ................ | A24F 47/004 131/329 |
| 2016/0007653 A1 | 1/2016 | Tu | |
| 2016/0044960 A1 | 2/2016 | O'Connor | |
| 2016/0100624 A1 | 4/2016 | Yilmaz et al. | |
| 2016/0166786 A1 | 6/2016 | Kinzer | |
| 2016/0171164 A1 | 6/2016 | Kinzer | |
| 2016/0183589 A1 | 6/2016 | Born et al. | |
| 2016/0271347 A1 | 9/2016 | Raichman | |
| 2016/0286860 A1 | 10/2016 | Flayler | |
| 2016/0295922 A1* | 10/2016 | John ................... | A24F 47/008 |
| 2016/0331022 A1 | 11/2016 | Cameron | |
| 2016/0331913 A1 | 11/2016 | Bourque | |
| 2017/0106153 A1 | 4/2017 | Davidson et al. | |
| 2017/0119979 A1 | 5/2017 | Davidson et al. | |

(56) References Cited

U.S. PATENT DOCUMENTS

| | | | |
|---|---|---|---|
| 2017/0119981 A1 | 5/2017 | Davidson et al. | |
| 2017/0127727 A1 | 5/2017 | Davidson et al. | |
| 2017/0136196 A1 | 5/2017 | Davidson et al. | |
| 2017/0150755 A1* | 6/2017 | Batista | A24F 47/008 |
| 2017/0157343 A1 | 6/2017 | Davidson et al. | |
| 2017/0164657 A1* | 6/2017 | Batista | A24F 47/008 |
| 2017/0203058 A1 | 7/2017 | Davidson et al. | |
| 2017/0360089 A1 | 12/2017 | Davidson et al. | |

FOREIGN PATENT DOCUMENTS

| | | | |
|---|---|---|---|
| EP | 2292108 | 3/2011 | |
| GB | 2108390 | 5/1983 | |
| GB | 2340758 | 3/2000 | |
| GB | 2495771 | 4/2013 | |
| WO | WO 9409842 A1 * | 5/1994 | A61M 15/0028 |
| WO | WO 98/04308 | 2/1998 | |
| WO | WO 00/24362 | 5/2000 | |
| WO | WO 03/037412 | 5/2003 | |
| WO | WO 2005/061033 | 7/2005 | |
| WO | WO 2008/024408 | 2/2008 | |
| WO | WO 2008/024490 | 2/2008 | |
| WO | WO 2008/116165 | 9/2008 | |
| WO | WO 2009/124552 | 10/2009 | |
| WO | WO 2010/015260 | 2/2010 | |
| WO | WO 2011/073306 | 6/2011 | |
| WO | WO 2012/006125 | 1/2012 | |
| WO | WO 2012/006126 | 1/2012 | |
| WO | WO 2012/026963 | 3/2012 | |
| WO | WO 2012/085919 | 6/2012 | |
| WO | WO 2013/057185 | 4/2013 | |
| WO | WO 2013/083636 | 6/2013 | |
| WO | WO 2014061477 A1 * | 4/2014 | A24F 47/004 |
| WO | WO 2015/123064 | 8/2015 | |
| WO | WO 2015/123317 | 8/2015 | |
| WO | WO 2015/175979 | 11/2015 | |
| WO | WO 2016/001921 | 1/2016 | |
| WO | WO 2016/001922 | 1/2016 | |
| WO | WO 2016/001923 | 1/2016 | |
| WO | WO 2016/001924 | 1/2016 | |
| WO | WO 2016/001925 | 1/2016 | |
| WO | WO 2016/001926 | 1/2016 | |
| WO | WO 2016/090303 | 6/2016 | |
| WO | WO 2016/147188 | 9/2016 | |
| WO | WO 2016/172802 | 11/2016 | |
| WO | WO 2016/187696 | 12/2016 | |
| WO | WO 2017/118980 | 7/2017 | |

OTHER PUBLICATIONS

International Preliminary Report on Patentability dated Jul. 2, 2013 From the International Preliminary Examining Authority Re. Application No. PCT/IL2011/050071.
International Preliminary Report on Patentability dated Jan. 12, 2017 From the International Bureau of WIPO Re. Application No. PCT/IL2015/050674. (11 Pages).
International Preliminary Report on Patentability dated Jan. 12, 2017 From the International Bureau of WIPO Re. Application No. PCT/IL2015/050675. (8 Pages).
International Preliminary Report on Patentability dated Jan. 12, 2017 From the International Bureau of WIPO Re. Application No. PCT/IL2015/050677. (13 Pages).
International Preliminary Report on Patentability dated Jan. 12, 2017 From the International Bureau of WIPO Re. Application No. PCT/IL2015/050678. (12 Pages).
International Search Report and the Written Opinion dated Oct. 19, 2012 From the International Searching Authority Re. Application No. PCT/IL2011/050071.
Office Action dated Jan. 19, 2017 From the Israel Patent Office Re. Application No. 227102 and Its Translation Into English. (5 Pages).
Office Action dated Jun. 22, 2016 From the Israel Patent Office Re. Application No. 227102 and Its Translation Into English.
Official Action dated Jan. 30, 2017 From the US Patent and Trademark Office Re. U.S. Appl. No. 13/997,302. (23 pages).
Official Action dated Sep. 30, 2016 From the US Patent and Trademark Office Re. U.S. Appl. No. 13/997,302.
Restriction Official Action dated Jul. 8, 2016 From the US Patent and Trademark Office Re. U.S. Appl. No. 13/997,302.
Written Opinion dated Apr. 22, 2013 From the International Preliminary Examining Authority Re. Application No. PCT/IL2011/050071.
Official Action dated Mar. 9, 2017 From the US Patent and Trademark Office Re. U.S. Appl. No. 15/386,182. (24 pages).
Official Action dated Mar. 13, 2017 From the US Patent and Trademark Office Re. U.S. Appl. No. 15/391,896. (22 pages).
Notice of Allowance dated Jun. 1, 2017 From the US Patent and Trademark Office Re. U.S. Appl. No. 13/997,302. (24 Pages).
Official Action dated Jun. 1, 2017 From the US Patent and Trademark Office Re. U.S. Appl. No. 15/375,098. (42 pages).
Jang et al. "Thermophysical Properties of Porous SiC Ceramics Fabricated by Pressureless Sintering", Science and Technology of Advanced Materials, 8(7): 655-659, Nov. 30, 2007.
Norwood et al. "Best Practices for Extractables and Leachables in Orally Inhaled and Nasal Drug Products: An Overview of the PQRI Recommendations", Pharmaceutical Research, 25(4): 727-739, Published Online Jan. 9, 2008.
Communication Pursuant to Article 94(3) EPC dated Jun. 23, 2017 From the European Patent Office Re. Application No. 11815728.8. (5 Pages).
Ibrahim et al. "Inhalation Drug Delivery Devices: Technology Update", Medical Devices: Evidence and Research, 8: 131-139, Feb. 12, 2015.
Lanz et al. "Medicinal Cannabis: In Vitro Validation of Vaporizers for the Smoke-Free Inhalation of Cannabis", PLOS ONE, 11(1): e0147286-1-e0147286-18, Jan. 19, 2016.
Pomahacova et al. "Cannabis Smoke Condensate III: The Cannabinoid Content of Vaporised Cannabis Sativa", Inhalation Toxicology, 21(13): 1108-1112, Nov. 1, 2009.
International Search Report and the Written Opinion dated Mar. 27, 2017 From the International Searching Authority Re. Application No. PCT/IL2017/050014. (16 Pages).
Official Action dated Apr. 6, 2017 From the US Patent and Trademark Office Re. U.S. Appl. No. 15/362,841. (35 pages).
Official Action dated Apr. 10, 2017 From the US Patent and Trademark Office Re. U.S. Appl. No. 15/362,883. (33 pages).
Official Action dated Apr. 20, 2017 From the US Patent and Trademark Office Re. U.S. Appl. No. 15/382,819. (30 pages).
Applicant-Initiated Interview Summary dated May 22, 2017 From the US Patent and Trademark Office Re. U.S. Appl. No. 15/386,182. (3 pages).
Applicant-Initiated Interview Summary dated May 23, 2017 From the US Patent and Trademark Office Re. U.S. Appl. No. 15/362,841. (3 pages).
Applicant-Initiated Interview Summary dated May 23, 2017 From the US Patent and Trademark Office Re. U.S. Appl. No. 15/362,883. (3pages).
Applicant-Initiated Interview Summary dated May 23, 2017 From the US Patent and Trademark Office Re. U.S. Appl. No. 15/375,098. (3 pages).
Applicant-Initiated Interview Summary dated May 23, 2017 From the US Patent and Trademark Office Re. U.S. Appl. No. 15/382,819. (3 pages).
International Preliminary Report on Patentability dated Jan. 12, 2017 From the International Bureau of WIPO Re. Application No. PCT/IL2015/050673. (15 Pages).
International Preliminary Report on Patentability dated Jan. 12, 2017 From the International Bureau of WIPO Re. Application No. PCT/IL2015/50676. (11 Pages).
Communication Relating to the Results of the Partial International Search dated Oct. 22, 2015 From the International Searching Authority Re. Application No. PCT/IL2015/050673.
Communication Relating to the Results of the Partial International Search dated Sep. 24, 2015 From the International Searching Authority Re. Application No. PCT/IL2015/050677.

(56) References Cited

OTHER PUBLICATIONS

International Search Report and the Written Opinion dated Feb. 2, 2016 From the International Searching Authority Re. Application No. PCT/IL2015/050673.
International Search Report and the Written Opinion dated Dec. 3, 2015 From the International Searching Authority Re. Application No. PCT/IL2015/050677.
International Search Report and the Written Opinion dated Jan. 7, 2016 From the International Searching Authority Re. Application No. PCT/IL2015/050675.
International Search Report and the Written Opinion dated Dec. 10, 2015 From the International Searching Authority Re. Application No. PCT/IL2015/050674.
International Search Report and the Written Opinion dated Jan. 20, 2016 From the International Searching Authority Re. Application No. PCT/IL2015/50676.
International Search Report and the Written Opinion dated Oct. 22, 2015 From the International Searching Authority Re. Application No. PCT/IL2015/050678.
AAAAI "Inhaled Asthma Medications: Tips to Remember", American Academy of Allergy Asthma & Immunology, AAAAI, 4 P., 2013.
Abrams et al. "Vaporization as A Smokeless Cannabis Delivery System: A Pilot Study", Clinical Pharmacology & Therapeutics, 82(5): 572-578, Advance Online Publication Apr. 11, 2007.
Bhattacharyya et al. "Opposite Effects of Delta-9-Tetrahydrocannabinol and Cannabidiol on Human Brain Function and Psychopathology", Neuropsychopharmacology, 35: 764-774, 2010.
Boden et al. "The Effects of Cannabis Use Expectancies on Self-Initiated Cannabis Cessation", Addiction, 108: 1649-1657, 2013.
Das et al. "Effects of 9-Ene-Tetrahydrocannabinol on Expression of Beta-Type Transforming Growth Factors, Insulin-Like Growth Factor-I and C-Myc Genes in the Mouse Uterus", The Journal of Steroid Biochemistry and Molecular Biology, 45(6): 459-465, 1993.
Eisenberg et al. "The Pharmacokinetics, Efficacy, Safety, and Ease of Use of A Novel Portable Metered-Dose Cannabis Inhaler in Patients With Chronic Neuropathic Pain: A Phase 1a Study", Journal of Pain & Palliative Care Pharmacotherapy, 28(3): 216-225, Published Online Aug. 13, 2014.
Farrimond et al. "Cannabinol and Cannabidiol Exert Opposing Effects on Rat Feeding Patterns", Psychopharmacology, 223: 117-129, 2012.
FDA "Guidance for Industry. Population Pharmacokinetics", U.S. Department of Health and Human Services, Food and Drug Administration (FDA), Center for Drug Evaluation and Research (CDER), Center for Biological Evaluation and Research (CBER), CP 1: 1-31, Feb. 1999.
Hazekamp et al. "Bedrocan®—Stimulating the Development of Herbal Cannabis-Based Products", Bedromedical Presentation, 2013.
Hazekamp et al. "Evaluation of A Vaporizing (Volcano®) for the Pulmonary Administration of Tetrahydrocannabinol", Journal of Pharmaceutical Sciences, 95(6): 1308-1317, Jun. 2006.
Hazekamp et al. "The Medicinal Use of Cannabis and Cannabinoids—An International Cross-Sectional Survey on Administration Forms", Journal of Psychoactive Drugs, 45(3): 199-210, 2013.
Herbalizer "Herbalizer, the New Vaporization Experience", 6 P., Jun. 7, 2013.
Jamontt et al. "The Effects of Delta[9]-Tetrahydrocannabinol and Cannabidiol Alone and in Combination on Damage, Inflammation and In Vitro Motility Disturbances in Rat Colitis", British Journal of Pharmacology, 160: 712-723, 2010.
McPartland et al. "Are Cannabidiol and Delta9-Tetrahydrocannabivarin Negative Modulators of the Endocannabinoid System? A Systematic Review", British Journal of Pharmacology, 172(3): 737-753, Published Online Jan. 8, 2015.
Mechoulam et al. "Cannabidiol—Recent Advances", Chemistry & Biodiversity, 4: 1678-1692, 2007.
Pertwee "The Diverse CB1 and CB2 Receptor Pharmacology of Three Plant Cannabinoids: Delta[9]-Tetrahydrocannabinol, Cannabidiol and Delta[9]-Tetrahydrocannabivarin", British Journal of Pharmacology, 153: 199-215, 2008.
Rabinowitz et al., "Fast Onset Medications Through Thermally Generated Aerosols", The Journal of Pharmacological and Experimental Therapeutics, 309(2): 769-775, 2004.
Rau "The Inhalation of Drugs: Advantages and Problems", Respiratory Care, 50(3): 367-382, Mar. 2005.
Strougo et al. "Modelling of the Concentration—Effect Relationship of THC on Central Nervous System Parameters and Heart Rate—Insight Into Its Mechanisms of Action and a Tool for Clinical Research and Development of Cannabinoids", Journal of Pharmacology, 22(7): 717-726, Sep. 2008.
Syqe Medical "The World's First Metered Dose Pharmaceutical Grade Medical Cannabis Inhaler", Syqe Medical™, Press Kit, p. 1-8, 2015.
Van Gerven "Biomarkers to Assess Adverse Drug Effects on the CNS", Centre for Human Drug Research, CHDR, Poster-Session, Slide-Show, 25 P., 2013.
Van Hell et al. "Evidence for Involvement of the Insula in the Psychotropic Effects of THC in Humans: A Double-Blind, Randomized Pharamcological MRI Study", International Journal of Neuropharmacology, 14: 1377-1388, 2011.
Vann et al. "Divergent Effects of Cannabidiol on the Discriminative Stimulus and Place Conditioning Effects of Delta 9-Tetrahydrocannabiol", Drug and Alcohol Dependence, 94(1-3): 191-198, Apr. 1, 2008.
Vemuri et al. "Pharmacotherapeutic Targeting of the Endocannabinoid Signaling System: Drugs for Obesity and the Metabolic Syndrome", Physiology & Behavior, 93: 671-686, 2008.
Wallace et al. "Efficacy of Inhaled Cannabis on Painful Diabetic Neuropathy", The Journal of Pain, 169(7): 616-627, Published Online Apr. 3, 015.
Ware et al. "Smoked Cannabis for Chronic Neuropathic Pain: A Randomized Controlled Trial", Canadian Medical Association Journal, CMAJ, 182(14): E694-E701, Published Online Aug. 30, 2010.
Wilsey et al. "Low-Dose Vaporized Cannabis Significantly Improves Neuropathic Pain", The Journal of Pain, 14(2): 136-148, Published Online Dec. 13, 2012.
Zuurman et al. "Biomarkers for the Effects of Cannabis and THC in Healthy Volunteers", British Journal of Clinical Pharmacology, 67(1): 5-21, 2008.
Zuurman et al. "Effect of Intrapulmonary Tetrahydrocannabinol Administration in Humans", Journal of Psychopharmacology, 22(7): 707-716, 2008.
Examiner-Initiated Interview Summary dated Nov. 2, 2017 From the US Patent and Trademark Office Re. U.S. Appl. No. 15/382,819. (2 pages).
Official Action dated Nov. 1, 2017 From the US Patent and Trademark Office Re. U.S. Appl. No. 15/382,819. (45 pages).
Official Action dated Sep. 22, 2017 From the US Patent and Trademark Office Re. U.S. Appl. No. 15/362,883. (43 pages).
Official Action dated Sep. 28, 2017 From the US Patent and Trademark Office Re. U.S. Appl. No. 15/312,647. (57 pages).
Restriction Official Action dated Aug. 7, 2017 From the US Patent and Trademark Office Re. U.S. Appl. No. 15/312,647. (8 pages).
Communication Pursuant to Article 94(3) EPC dated Jan. 19, 2018 From the European Patent Office Re. Application No. 15744363.1. (4 Pages).
Communication Pursuant to Article 94(3) EPC dated Jan. 22, 2018 From the European Patent Office Re. Application No. 15756490.7. (4 Pages).
Communication Pursuant to Article 94(3) EPC dated Feb. 26, 2018 From the European Patent Office Re. Application No. 15753782.0. (6 Pages).
Official Action dated Mar. 14, 2018 From the US Patent and Trademark Office Re. U.S. Appl. No. 15/362,883. (21 pages).
Supplementary European Search Report and the European Search Opinion dated Mar. 19, 2018 From the European Patent Office Re. Application No. 15814472.5. (9 Pages).
Assaf et al. "Pre- And Post-Conditioning Treatment With an Ultra-Low Dose of [Delta]$^9$-Tetrahydrocannabinol (THC) Protects

(56) References Cited

OTHER PUBLICATIONS

Against Pentylenetetrazole (PTZ)-Induced Cognitive Damage", Behavioral Brain Research, 220(1): 194-201, Jun. 2011.

Fishbein et al. "Long-Term Behavioral and Biochemical Effects of an Ultra-Low Dose of [Delta]$^{sup9}$-Tetrahydrocannabinol (THC): Neuroprotection and ERK Signaling", Experimental Brain Research, 221(4): 437-448, Published Online Jul. 22, 2012.

Applicant-Initiated Interview Summary dated Apr. 5, 2018 From the US Patent and Trademark Office Re. U.S. Appl. No. 15/391,896. (3 pages).

Communication Pursuant to Article 94(3) EPC dated Apr. 26, 2018 From the European Patent Office Re. Application No. 11815728.8. (4 Pages).

Supplementary European Search Report and the European Search Opinion dated Mar. 19, 2018 From the European Patent Office Re. Application No. 15815982.2. (8 Pages).

Applicant-Initiated Interview Summary dated Jan. 5, 2018 From the US Patent and Trademark Office Re. U.S. Appl. No. 15/382,819. (3 pages).

Applicant-Initiated Interview Summary dated Dec. 22, 2017 From the US Patent and Trademark Office Re. U.S. Appl. No. 15/312,647. (3 pages).

Applicant-Initiated Interview Summary dated Dec. 22, 2017 From the US Patent and Trademark Office Re. U.S. Appl. No. 15/362,883. (3 pages).

Office Action dated Dec. 21, 2017 From the Israel Patent Office Re. Application No. 227102 and Its Translation Into English. (4 Pages).

Official Action dated Jan. 25, 2018 From the US Patent and Trademark Office Re. U.S. Appl. No. 15/375,098. (37 pages).

Official Action dated Dec. 26, 2017 From the US Patent and Trademark Office Re. U.S. Appl. No. 15/391,896. (53 pages).

Requisition by the Examiner dated Nov. 16, 2017 From the Innovation, Science and Economic Development Canada, Canadian Intellectual Property Office Re. Application No. 2,822,738. (4 Pages).

International Preliminary Report on Patentability dated Jul. 19, 2018 From the International Bureau of WIPO Re. Application No. PCT/IL2017/050014. (10 Pages).

Carter et al. "Medicinal Cannabis: Rational Guidelines for Dosing", IDrugs, 7(5): 464-470, May 2004.

\* cited by examiner

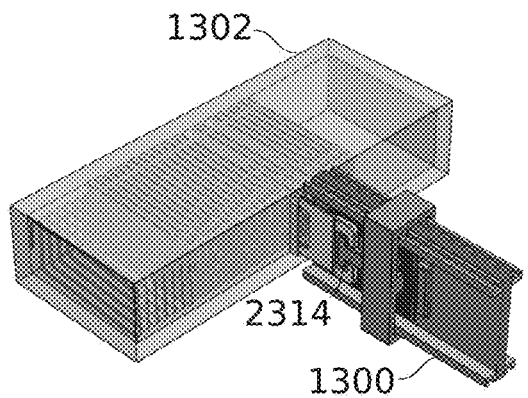
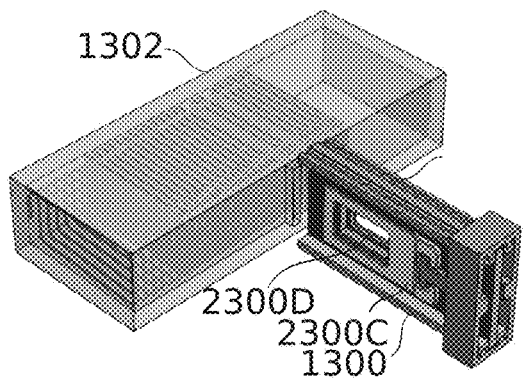
FIG. 13A    FIG. 13B
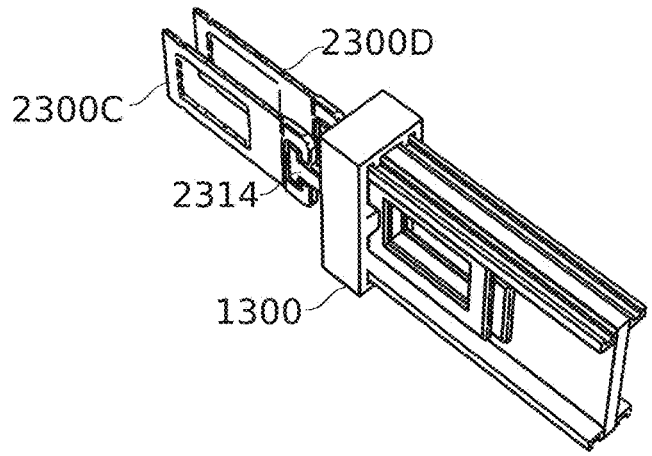
FIG. 13C
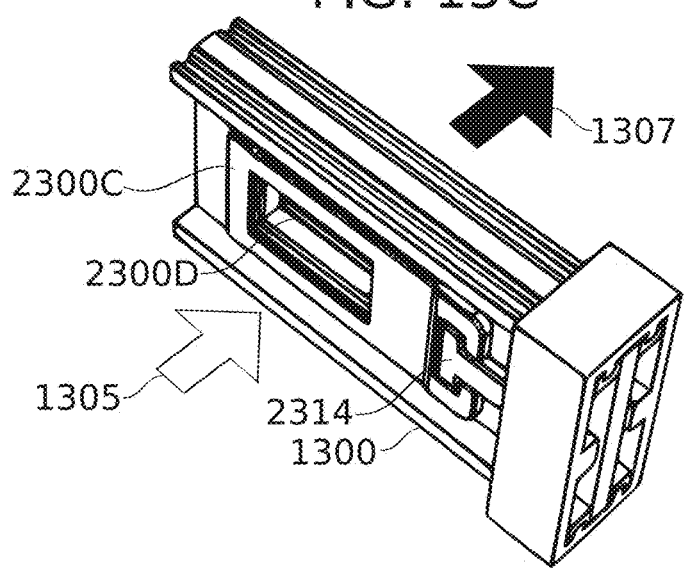
FIG. 13D

DRUG DOSE CARTRIDGE FOR AN INHALER DEVICE

RELATED APPLICATIONS

This application is a National Phase of PCT Patent Application No. PCT/IL2015/050677 having International filing data Jun. 30, 2015, which claims the benefit of priority under 35 USC § 119(e) of U.S. Provisional Patent Application No. 62/019,225 filed on Jun. 30, 2014; U.S. Provisional Patent Application No. 62/035,588 filed on Aug. 11, 2014; U.S. Provisional Patent Application No. 62/085,772 filed on Dec. 1, 2014; U.S. Provisional Patent Application No. 62/086,208 filed on Dec. 2, 2014; and U.S. Provisional Patent Application No. 62/164,710 filed on May 21, 2015.

PCT Patent Application No. PCT/IL/2015/050677 was co-filed on Jun. 20, 2015 together with PCT Patent Application Nos. PCT/IL2015/050673, PCT/IL2015/050678, PCT/IL2015/050676, PCT/IL2015/050674, and PCT/IL2015/050675. The contents of the above applications are all incorporated by reference as if fully set forth herein in their entirety.

FIELD AND BACKGROUND OF THE INVENTION

The present disclosure, in some embodiments thereof, relates to pulmonary delivery of a substance using a personal inhaler device and, more particularly, but not exclusively, to dosage manufacture and handling for administration.

U.S. Pat. No. 5,655,520 teaches: "A nebulizer is improved by placing a flexible valve in the ambient air inlet tube. Inhalation suction and Venturi effect shut down the flexible valve in proportion to the strength of the inhalation. Thus, the same output flow rate is obtained even with variable strength inhalations. Medications can be properly administered by controlled inhalation flow rates. In an alternate embodiment a metered dose inhaler (MDI) is outfitted with a similar flexible valve. Once again the patient is forced to inhale at a constant flow rate, thus causing the medication to seep deeply into the lungs. In both embodiments the flexible valve is preferably shaped in a duck billed fashion with air flow flowing toward the narrow end of the duck bill."

SUMMARY OF THE INVENTION

According to an aspect of some embodiments, there is provided a dose cartridge for an inhaler device, the dose cartridge comprising: a flat pallet of airflow-permeable material including a heat-vaporizing drug substance, the pallet having two opposing faces and being positioned in the dose cartridge so as to expose the two faces to airflow; a supporting member coupled to the pallet to support the pallet from at least one side of the pallet joining the two faces; and an electrically resistive heating element extending at least partially across at least one of the two opposing faces from an attachment with the supporting member.

According to some embodiments, the supporting member frames at least a portion of at least three sides of the pallet.

According to some embodiments, the supporting member extends between the two faces of the pallet along an edge of the pallet.

According to some embodiments, the resistive heating element is in thermal contact with and extends across at least two opposite surfaces of the pallet.

According to some embodiments, the resistive heating element comprises a U-shape with two ends around a hollow in which the pallet is positioned.

According to some embodiments, an electrical current flows across the two opposite surfaces when a voltage is applied between the two ends.

According to some embodiments, the resistive heating element comprises at least two resistive heating elements, wherein each resistive heating element is in thermal contact with and extends across at least a portion of the pallet.

According to some embodiments, the at least two resistive heating elements extend across opposite surfaces of the pallet.

According to some embodiments, the resistive heating element has a portion encased and extending within at least a portion of the pallet.

According to some embodiments, the resistive heating element extends across a surface of the pallet, and comprises a plurality of protrusions into the pallet.

According to some embodiments, at least a portion of the resistive heating element extending across the pallet is permeable to the passage of air.

According to some embodiments, a portion of the resistive heating element extending across the pallet comprises a barrier which prevents a granulate portion of the pallet from leaving the inhaler dose cartridge.

According to some embodiments, the resistive heating unit comprises a woven mesh.

According to some embodiments, the resistive heating unit comprises at least one ribbon of etched metal foil.

According to some embodiments, the at least one ribbon of etched metal foil is backed by a polymer backing comprising a plurality of perforations making it permeable to the passage of air.

According to some embodiments, the at least one ribbon of etched metal foil comprises a narrowed region having elevated resistance, which melts to break electrical continuity along the at least one ribbon during dissipation of electrical power applied after release the heat-vaporizing drug substance.

According to some embodiments, the at least one ribbon of etched metal foil is attached to a fuse element configured to break electrical continuity along the at least one ribbon during dissipation of electrical power applied after release the heat-vaporizing drug substance.

According to some embodiments, at least a portion of the resistive heating element is embedded in the pallet.

According to some embodiments, the air-permeable support member is sufficiently closed to prevent a granulate portion of the pallet from leaving the inhaler dose cartridge.

According to some embodiments, the air-permeable support member separates the pallet and the heating element.

According to some embodiments, the material comprises *cannabis*.

According to some embodiments, the material comprises at least one botanical substance selected from the group consisting of *Cannabis sativa, Cannabis indica, Cannabis ruderalis, Acacia* spp., *Amanita muscaria*, Yage, *Atropa belladonna, Areca catechu, Brugmansia* spp., *Brunfelsia latifolia, Desmanthus illinoensis, Banisteriopsis caapi, Trichocereus* spp., *Theobroma cacao, Capsicum* spp., *Cestrum* spp., *Erythroxylum coca, Solenostemon scutellarioides, Arundo donax, Coffea arabica, Datura* spp., *Desfontainia* spp., *Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper* methysticum, Catha edulis, Mitragyna speciosa, Leonotis leonurus, Nymphaea spp., Nelumbo spp., Sophora secundiflora, Mucuna pruriens, Mandragora officinarum, Mimosa tenuiflora, Ipomoea violacea, Psilocybe spp., Panaeolus spp., Myristica fragrans, Turbina corymbosa, Passiflora incarnata, Lophophora williamsii, Phalaris spp., Duboisia hopwoodii, Papaver somniferum, Psychotria viridis, spp., Salvia divinorum, Combretum quadrangulare, Trichocereus pachanoi, Heimia salicifolia, Stipa robusta, Solandra spp., Hypericum perforatum, Peganum harmala, Tabernaemontana spp., Camellia sinensis, Nicotiana tabacum, Nicotiana rustica, Virola theidora, Voacanga africana, Lactuca virosa, Artemisia absinthium, Ilex paraguariensis, Anadenanthera spp., Corynanthe yohimbe, Calea zacatechichi, Coffea spp. (Rubiaceae), Sapindaceae spp., Camellia spp., Malvaceae spp., Aquifoliaceae spp., Hoodia spp. Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis, Tobacco, Aloe Vera, Angelica, Anise, Ayahuasca (Banisteriopsis caapi), Barberry, Black Horehound, Blue Lotus, Burdock, Camomille/Chamomile, Caraway, Cat's Claw, Clove, Comfrey, Corn Silk, Couch Grass, Damiana, Damiana, Dandelion, Ephedra, Eucalyptus, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, Sida Cordifolia, Sinicuichi (Mayan Sun Opener), Spearmint, Sweet Flag, Syrian Rue (Peganum harmala), Thyme, Turmeric, Valerian, Wild Yam, Wormwood, Yarrow, Yerba Mate, and Yohimbe.

According to some embodiments, the electrically resistive heating element comprises an electrode contact-receiving region on either side of a region extending across the pallet.

According to some embodiments, the inhaler dose cartridge comprises a plurality of heating element regions, each region being separately configured to receive electric current.

According to some embodiments, the plurality of heating elements is associated with a corresponding plurality of pallets.

According to some embodiments, the resistive heating element comprises an attachment element, shaped for attachment to the transport arm of a dose puller.

According to some embodiments, at least a portion of the dose cartridge is configured to allow a flow through the pallet at a rate of at least 0.5 liters of gas per minute under a pulling vacuum of at least 1 kPa.

According to some embodiments, the supporting member is surrounded by the pallet where it extends between the two faces of the pallet.

According to some embodiments, the supporting member comprises a hollow region open on at least one of the two faces.

According to some embodiments, the resistive heating element is a metal resistive heating element.

According to an aspect of some embodiments, there is provided a method of manufacturing an inhaler dose cartridge for pulmonary delivery of a heat-vaporizing drug substance, comprising: preparing a pallet of material comprising the heat-vaporizing drug substance; attaching the pallet to a supporting member extending between the two faces of the pallet; and attaching an electrically resistive heating element to the pallet.

According to some embodiments, the preparing the pallet comprises: placing a granulated botanical substance within a dose chamber on a planar surface; and leveling the botanical substance within the dose chamber.

According to some embodiments, preparing the pallet comprises: placing a granulated botanical substance within a dose chamber on a planar surface; vibrating the planar surface until the granulated botanical substance is leveled; and pressing the leveled botanical substance, reducing the volume thereof by at least 50% to form a pallet.

According to some embodiments, preparing the pallet comprises cutting a tape section from a botanical substance formed into a tape.

According to some embodiments, preparing the pallet comprises loading an air permeable granulated botanical material with a gel, fluid or powder comprising the heat-vaporizing drug substance.

According to some embodiments, the material comprises cannabis.

According to some embodiments, the material comprises at least one botanical substance selected from the group consisting of Cannabis sativa, Cannabis indica, Cannabis ruderalis, Acacia spp., Amanita muscaria, Yage, Atropa belladonna, Areca catechu, Brugmansia spp., Brunfelsia latifolia, Desmanthus illinoensis, Banisteriopsis caapi, Trichocereus spp., Theobroma cacao, Capsicum spp., Cestrum spp., Erythroxylum coca, Solenostemon scutellarioides, Arundo donax, Coffea arabica, Datura spp., Desfontainia spp., Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea spp., Nelumbo spp., Sophora secundiflora, Mucuna pruriens, Mandragora officinarum, Mimosa tenuiflora, Ipomoea violacea, Psilocybe spp., Panaeolus spp., Myristica fragrans, Turbina corymbosa, Passiflora incarnata, Lophophora williamsii, Phalaris spp., Duboisia hopwoodii, Papaver somniferum, Psychotria viridis, spp., Salvia divinorum, Combretum quadrangulare, Trichocereus pachanoi, Heimia salicifolia, Stipa robusta, Solandra spp., Hypericum perforatum, Peganum harmala, Tabernaemontana spp., Camellia sinensis, Nicotiana tabacum, Nicotiana rustica, Virola theidora, Voacanga africana, Lactuca virosa, Artemisia absinthium, Ilex paraguariensis, Anadenanthera spp., Corynanthe yohimbe, Calea zacatechichi, Coffea spp. (Rubiaceae), Sapindaceae spp., Camellia spp., Malvaceae spp., Aquifoliaceae spp., Hoodia spp. Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis, Tobacco, Aloe Vera, Angelica, Anise, Ayahuasca (Banisteriopsis caapi), Barberry, Black Horehound, Blue Lotus, Burdock, Camomille/Chamomile, Caraway, Cat's Claw, Clove, Comfrey, Corn Silk, Couch Grass, Damiana, Damiana, Dandelion, Ephedra, Eucalyptus, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, Sida Cordifolia, Sinicuichi (Mayan Sun Opener), Spearmint, Sweet Flag, Syrian Rue (*Peganum harmala*), Thyme, Turmeric, Valerian, Wild Yam, Wormwood, Yarrow, Yerba Mate, and Yohimbe.

According to some embodiments, the granulated botanical substance comprises botanical substance having maintained its microstructure intact.

According to some embodiments, the preparing a pallet comprises freezing a botanical substance, and grinding the frozen botanical substance to granulate it, wherein the grinding is substantially without breaking the microstructure of the botanical substance.

According to some embodiments, the unbroken microstructure comprises at least 90% of vacuoles containing the drug substance remaining unbroken after granulation.

According to some embodiments, preparing the pallet comprises loading an air permeable material with a gel, fluid or powder comprising the heat-vaporizing drug substance.

According to some embodiments, the attaching the pallet to a supporting member is performed during formation of the pallet.

According to an aspect of some embodiments, there is provided an inhaler dose cartridge for pulmonary delivery of a heat-vaporizing drug substance to a user comprising: an airflow-permeable pallet of a material comprising the heat-vaporizing drug, wherein the pallet is oriented within the dose cartridge such that it is subjected to airflow through the pallet between two face surfaces of thereof; a supporting member extending between the two faces of the pallet; and an airflow permeable retaining element extending across at least one of the two face surfaces and connected to the supporting member.

According to some embodiments, the material of the pallet comprises friable material.

According to some embodiments, the friable material comprises botanical substance having intact microstructure of the natural botanical substance.

According to some embodiments, the inhaler dose cartridge comprises an electrically resistive heating element in thermal communication with the pallet.

According to some embodiments, the electrically resistive heating element extends across at least one of the two face surfaces.

According to some embodiments, the airflow permeable retaining element comprises the electrically resistive heating element.

According to some embodiments, the inhaler dose cartridge comprises a frame element which at least partially surrounds the pallet on one or more sides adjacent to the retaining element.

According to some embodiments, the frame element comprises an aperture into which the pallet of material is fittingly pressed.

According to some embodiments, the frame element comprises a polymer resistant to heat at the temperature at which the heat-vaporizing drug substance vaporizes.

According to some embodiments, the frame element is attached to the resistive heating element by at least partial melting of the polymer frame, such that material of the polymer frame flows into one or more apertures in the resistive heating element.

According to some embodiments, the electrically resistive heating element is at least partially embedded in a portion of the frame element.

According to some embodiments, the electrically resistive heating element is at least partially embedded in the pallet.

According to some embodiments, the frame element comprises a transport arm interlock region, shaped for attachment to the transport arm of a dose puller.

According to an aspect of some embodiments, there is provided a clamping chamber for an inhaler dose cartridge for pulmonary delivery of a heat-vaporizing drug substance to a user comprising: a cartridge transport configured to move the inhaler dose cartridge from a storage position into a use position; a holder for holding a dose cartridge such that a heat-vaporizing drug substance is in sealed alignment with an air conduit of the clamping chamber; and electrodes positioned to be in electrical contact with at least two electrical contact receiving regions of an electrically resistive heating element of an inhaler dose cartridge in the clamping chamber.

According to some embodiments, the cartridge transport comprises a dose pulling arm, shaped to interlock with a receiving region of the dose cartridge such that movement of the dose pulling arm moves a dose cartridge into or out of the use position.

According to some embodiments, the sealed alignment defines a pathway through a pallet of material within a lumen along which air passing through the pallet continues to an exit aperture leading to the pulmonary organs of the user.

According to some embodiments, the holder comprises the cartridge transport configured to move the inhaler dose cartridge.

According to some embodiments, the clamping chamber comprises: a plurality of the cartridge transports each configured to move a corresponding inhaler dose cartridge; a plurality of holders corresponding to the plurality of cartridge transports; and corresponding electrodes for each of the cartridge transports.

According to some embodiments, the plurality of holders is positioned sequentially along the air conduit such that airflow through one of the held dose cartridges passes through the other.

According to some embodiments, the plurality of holders is positioned such that each holder receives a separate airflow.

According to some embodiments, the air conduit comprises a plurality of lumens corresponding to the plurality of holders, and each of the holders is positioned in a separate one of the plurality of lumens.

According to some embodiments, each of the holders is positioned in a shared lumen of the air conduit.

According to some embodiments, at least one of the holders is operable to position a blocker which at least partially blocks airflow through the position where a dose cartridge is held.

According to some embodiments, the cartridge transport is configured to move any a plurality of inhaler dose cartridges to one of the plurality of holders.

According to an aspect of some embodiments, there is provided an inhaler device comprising the clamping chamber above.

According to an aspect of some embodiments, there is provided an inhaler device comprising two or more of the clamping chambers above.

According to some embodiments, the inhaler device comprises a dose cartridge dispenser comprising a plurality of dose cartridges within a closed container.

According to some embodiments, the plurality of dose cartridges comprise dose cartridges differing in at least one from among the group consisting of drug substance amount, drug substance concentration, and drug substance composition.

According to some embodiments, the inhaler device comprises a controller configured to select a dose cartridge from the plurality of dose cartridges in accordance with a dosing regimen.

According to some embodiments, the controller is configured to adjust the dosing regimen according to a progress of the regimen.

According to an aspect of some embodiments, there is provided a dose cartridge dispenser comprising a plurality of dose cartridges within a closed container, and including an interlock which, after dispensing of a first dose cartridge from the container, prevents dispensing of a second dose cartridge from the container until the first dose cartridge is returned to the dispenser.

According to some embodiments, the dose cartridge is dispensed to a substance vaporizing unit, and the operation of the interlock comprises inserting the substance vaporizing unit into the dose cartridge dispenser.

According to an aspect of some embodiments, there is provided a vaporizer device, comprising: a compartment sized to fittingly receive a dose cartridge from a dose cartridge container while the vaporizer device is fitted to the dose cartridge container, and a power unit operable, while the vaporizer device is removed from the dose cartridge container, to deliver current to a heating element of the fittingly received dose cartridge, for volatilization of a volatilizing substance contained by the dose cartridge.

According to some embodiments, the vaporizer device includes the dose cartridge container, the dose cartridge container containing a plurality of the dose cartridges.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIGS. 13A-13B schematically illustrate a linear-type dose cartridge magazine and dual-dose cartridge transport in two sequential positions, according to some embodiments; and FIGS. 13C-13D schematically illustrate the dual-dose cartridge transport of FIGS. 13A-13B in two sequential positions, according to some embodiments.

DESCRIPTION OF SPECIFIC EMBODIMENTS OF THE INVENTION

Figure 1:
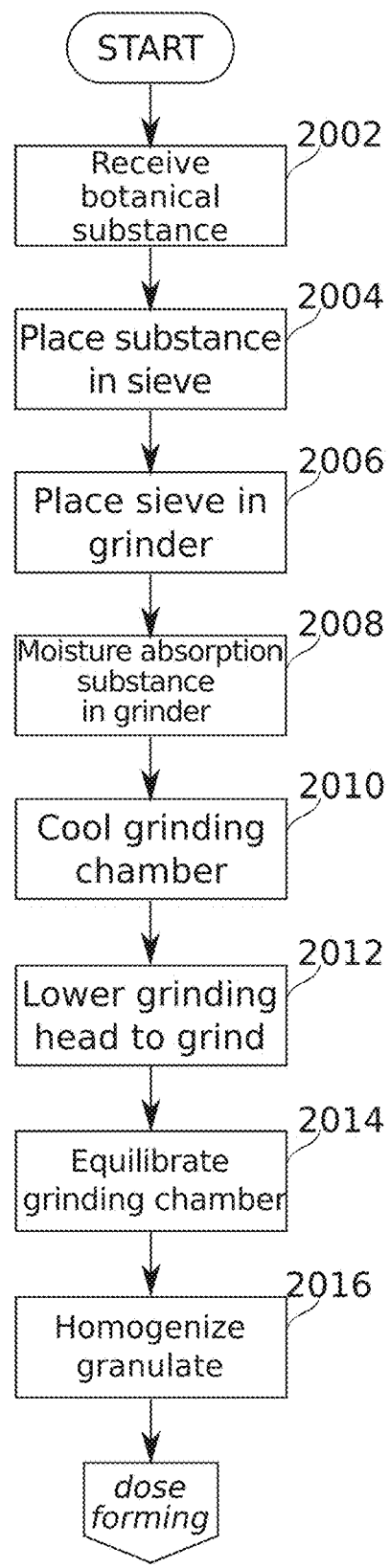
FIG. 1 is a schematic flowchart of a method of preparing a granulated botanical substance for use in dose packaging with an inhaler device, according to some embodiments.

The present disclosure, in some embodiments thereof, relates to pulmonary delivery of a substance using a personal inhaler device and, more particularly, but not exclusively, to dosage manufacture and handling for administration.

Overview

An aspect of some embodiments relates to processing and packaging of a heat-vaporizing drug substance to a cartridge providing an integrated heating element.

In some embodiments, the heat-vaporizing drug substance comprises a compound having at least one medicinal and/or somatic and/or psychoactive effect. Optionally the compound includes THC and/or nicotine. In some embodiments, the heat-vaporizing drug substance vaporizes at a temperature requiring a substantial exogenous heat input to reach a temperature above ambient temperature. For example, the substance vaporizes at a temperature within the range from 80° C.-250° C., or within another range having the same, higher, lower, intermediate and/or intermediate bounds. In some embodiments, the substance vaporizes at a temperature above 80° C., 100° C., 150° C., 200° C., 230° C., or another higher, lower, or intermediate temperature. In some embodiments, the time to reach a volatilizing temperature is, for example, about in a range between about 100 msec-5 sec, 100-750 msec, 150-300 msec, or another range having the same, larger, smaller, and/or intermediate bounds. In particular, the time is, for example, 250 msec, 500 msec, 1000 msec, or another greater, smaller, or intermediate value.

In some embodiments, the heat-vaporizing drug substance is a volatilizing substance distributed throughout a pallet comprising a carrier material. Optionally, the carrier material comprises at least one botanical substance, such as *cannabis*, tobacco, and/or other plant matter. Additionally or alternatively, the carrier material comprises a porous and air-permeable absorptive matrix; for example, a foam, sponge, felt, and/or another fiber matrix, which absorbs the heat-vaporizing drug substance to fix it into place. In some embodiments, the absorptive matrix is substantially non-friable, providing sufficient strength, for example, to allow direct attachment of other drug cartridge components, such as a heating element, to or within the absorptive matrix without a requirement for additional mechanical support to preserve the integrity of the absorptive matrix surfaces and/or structure. In some embodiments, the pallet is friable; for example, comprising granules, fibers, or another fine structure compressed to form the pallet.

In some embodiments, the heating element is an electrically resistive heating element. Optionally the electrically resistive heating element consists of or comprises a metal, for example nichrome, FeCrAl, cupronickel, titanium, and/or stainless steel. Optionally, the heating element is packaged in thermal contact with the heat-vaporizing drug substance. Thermal contact comprises, for example, being in direct contact, or in contact across a heat-transmitting layer allowing a high rate of thermal transfer (for example, comprised of a high heat conductance material such as copper, aluminum, brass or steel; and/or having a thin-walled construction of less than about 10 μm, 20 μm, 25 μm, 50 μm, or another greater, lesser or intermediate thickness). In some embodiments, thermal contact comprises sufficiently close apposition of pallet and heating element that the pallet subtends substantially the whole thermal radiating angle of the portion of the heating element overlying it; for example, more than 90%, 95%, 99%, or another greater, lesser or intermediate value. In some embodiments, the peak current applied to the electrode is in the range of about 1-10 Amperes; for example, about 1 Amperes, 2 Amperes, 4 Amperes, 6 Amperes, or another higher, lower, or intermediate current.

In some embodiments, the thermal contact comprises the heating element extending across and in contact with one or more surfaces of the pallet, for example, one side, or two opposite, largest surface-area sides of the pallet. In some embodiments, the thermal contact comprises the heating element being at least partially embedded within the pallet.

In some embodiments, the heating element is permeable to the passage of air. In some embodiments, the pallet is permeable to the passage of air. Permeability is under conditions, for example, of the passage of air at ambient temperature through a heated assembly of pallet and heating element under a suction pressure such as a suction pressure generated by inhaling, and/or a positive pressure generated from a side away from the inhaling side of the cartridge. In some embodiments, the applied pressure is in the range of 5-20 mmHg, 10-25 mmHg, 5-30 mmHg, 25-40 mmHg, 30-50 mmHg, or another range having the same, higher, lower, and/or intermediate bounds. According to some embodiments, the pallet has an air-permeable structure that allows a flow of at least 0.5 liters of gas per minute or even at least 1 liter of gas per minute under a pulling vacuum of at least 1-5 kPa (−1-(−5) kPa). In some embodiments, the pallet has this permeability in its packaged form. In some embodiments, this permeability is reached during heating of the pallet, for example, due to volatilization, drying, melting, and/or burning of the pallet constituents.

In some embodiments, the heating element comprises a bend of about 180°, such that the element is formed into a clip- and/or U-shape that encloses the pallet on at least two sides. Optionally, the heating element on the cartridge is positioned so that there is no self-contact between the two sides of the U-shape. Optionally, application of current to the heating element by a dose heating assembly is to or near the two ends (comprising contact-receiving regions) of the U-shape, such that heating may occur on two sides of the pallet at once. In some embodiments, application of current to the heating element is by connection to a contact-receiving region on either side of the pallet on one or both sides of the cartridge. The heating element is optionally divided into two or more parts, each receiving current independently. Alternatively, the heating element is provided as a single piece (optionally, a piece which entirely encloses the pallet); electrodes being applicable to contact-receiving regions of the element such that a voltage potential is generated over the extent of the heating element in thermal contact with the pallet.

An aspect of some embodiments relates to the providing of a support member along with the pallet and heating element.

In some embodiments, the support member comprises a frame, or a portion of a frame. Optionally, the frame comprises an aperture for receiving material of the pallet (a "dose chamber"). In some embodiments, the surface area over the width and length of the dose chamber is in the range of about 20-100 mm$^2$; for example, about 25 mm$^2$, 50 mm$^2$, 66 mm$^2$, 80 mm$^2$, 100 mm$^2$, or another greater, smaller, or intermediate surface area. In some embodiments, the aperture region is open on one side. Optionally, the open side of the aperture region is closed by the application of a U-shaped heating element.

In some embodiments, the frame aperture dimensions are, for example, about 6×10 mm, the frame defining a volume of, for example, about 0.5 mm or about 1 mm thick. In some embodiments, the ratio of a thickness of the pallet to a long or short side of the flat face of a pallet is about, for example, 1:5, 1:10, 1:12, 1:20, or another larger, smaller, or intermediate ratio. Optionally, the aperture area is in the range of about 20-100 mm$^2$; for example 20 mm$^2$, 40 mm$^2$, 50 mm$^2$, 60 mm$^2$, 80 mm$^2$, or another greater, lesser, or intermediate face area. The aperture is optionally shaped substantially as a square (for example, about 8×8 mm); optionally the aperture is oblong (for example, rectangular) with a side ratio of, for example, 1:2, 1:3, 1:4, 1:10, or another larger, smaller, or intermediate ration of side lengths. Optionally, the aperture is, for example, about 30×2 mm in dimension.

In some embodiments, the support member comprises a connection between structures which extend across one or both of the flattened faces of the pallet. For example, the support member is positioned at least partially around or alongside the pallet, and one or more other structures extends from an attachment to the support member across a flattened face of the pallet. Optionally, the support member extends at least partially within the body of the pallet itself. Optionally, the support member is attached on at least one side to an electrically resistive heating element, and/or a barrier permeable to airflow but configured to retain fragments of the pallet. In some embodiments, a support member provides a potential advantage for the containment of an optionally fragile pallet, by linking further supporting and/or enclosing structures to one another so that a space for containing the material of the pallet is defined without depending on the mechanical integrity of the pallet itself to hold together. In some embodiments, the support member extends along 1, 2, 3, or 4 sides of the pallet. Optionally, extending along four sides comprises an enclosing frame, while extent along fewer sides comprises a partially open frame which is optionally closed by another element of the chamber. Optionally, a support member extending along one side comprises an anchor through which elements of the cartridge are coupled to one another. In some embodiments, the support member avoids blocking exposure of the pallet to airflow by covering less than 20% of any of the flattened faces of the pallet. In some embodiments, the blocked exposure is less than 30%, less than 10%, less than 5%, or another greater, smaller, or intermediate amount.

In some embodiments, the support member and/or aperture performs one or more of the following functions:
- positions the pallet at a reproducible position relative to the overall dimensions of the cartridge;
- provides mechanical stability to the pallet (for example, support at one or more edges, rigidity to resist bending, and/or anchoring);
- provides attachment elements (e.g. latching/anchoring elements and/or surfaces) enabling the transport of the cartridge by mechanical elements shaped to interact with the cartridge;
- provides insulation between two parallel sides of the heating element to prevent self-contact; and/or
- provides surface region and/or bulk volume region for adherence/anchoring/embedding of the heating element with the cartridge.

In some embodiments, general functions of the frame and/or aperture include shaping of the dose structure during manufacture, and/or assistance in manipulation of the dose for administration.

In some embodiments, the material forming the pallet is friable. In some embodiments, for example, the pallet is formed from small adhering particles such a granulated botanical substance. While this is a potential advantage, for example, for increased porosity and/or to maintain microstructure of the original botanical substance (thus potentially helping to preserve drug substances from deterioration), the resulting structure is potentially fragile. In some embodiments, the maintained microstructure includes one or more of: cell walls, vacuole membranes, plastid membranes, trichome hairs and/or heads, or another plant microstructure, and in particular, a plant microstructure which encapsulates one or more drug substances. In some embodiments, at least 50% of a target microstructure (microstructure encapsulating a drug substance) is preserved during granulation. In some embodiments, the proportion of preserved target microstructure is at least 60%, 70%, 80%, 90%, 95%, 99%, or another larger, smaller, or intermediate proportion. In some embodiments, the pallet material is supported on one or both faces by a porous support structure, for example a mesh, perforated membrane, or another structure. The support structure is optionally porous enough to permit the passage of air, while still preventing the loss of particles from the friable pallet. In some embodiments, the pallet face support structure comprises a heating element. In some embodiments, the pallet face support structure comprises a polymer membrane, a fabric (for example, a woven mesh), or another flat, air-permeable support structure which covers the friable face of the pallet. In some embodiments, the pallet face support structure is positioned between the pallet and the heating element. Optionally, the heating element is positioned between the pallet and the pallet face support structure.

In some embodiments, the frame comprises a polymer or ceramic which is substantially heat resistant (for example, non-burning, non-melting, dimensionally stable) at the temperature of volatilization. In some embodiments, the polymer comprises, for example, a liquid crystal polymer (LCP), polyether ether ketone (PEEK), Ultem, Teflon, Torlon, Amodel, Ryton, Forton, Xydear, Radel, Udel, polypropylene, Propylux, polysulfone, polyether sulfone, acrylic, ABS, nylon, PLA, polybenzimadazole, polycarbonate, polyetherimide, polyethylene, polyphenylene oxide, polyphenylene sulfide, polystyrene, polyvinyl chloride, one or more other thermoplastics, and/or another polymer material.

In some embodiments, a latching/anchoring element comprises an attachment element (e.g. transport arm interlock region), shaped for attachment to the transport arm of a dose puller or other dose transport mechanism.

In some embodiments, the granulated portion of the pallet is closed within the assembled cartridge by the heating element extending across the aperture to form a barrier against the pallet granules falling from the cartridge. In some embodiments, the heating element extends across the aperture without itself closing the aperture (for example, a ribbon heating element is provided having gaps between windings of the ribbon). In some embodiments another element is provided which acts as a containment barrier (or wall). Optionally, the containment barrier is positioned over the heating element and pallet together, and/or between the heating element and the pallet.

An aspect of some embodiments relates to a method of manufacturing a drug dose load in the form of a pallet for assembly with an inhaler dose cartridge.

In some embodiments, a measured amount of a powdered or granulated material containing a drug substance (comprising, for example, a granulated botanical substance), is placed in a dose chamber. In some embodiments, the measured amount is in the range, for example, of about 10-100 mg. In some embodiments, the dose chamber is sized such that the extent of the dose pallet, upon formation, is limited by bounds of the dose chamber, for example, bounds of pallet width and length.

In some embodiments, the measured amount of granulated substance is leveled by vibration of the dose chamber. Optionally, the vibrating is with an amplitude in the range of about 0.1-1.2 mm; for example 0.5 mm. The frequency of vibration is, for example, in the range of about 20-300 Hz (such as 30 Hz, 45 Hz, 60 Hz, 75 Hz, or another higher, lower, or intermediate frequency). Duration of shaking is, for example, chosen from within the range of 100-1100 msec (such as about 300 msec, 400 msec, 500 msec, 800 msec, or another longer, shorter, or intermediate time). Optionally, the chamber is secured before vibration, to prevent granulate from escaping the chamber from underneath.

In some embodiments, leveling the measured amount of granulate substance comprises using a rigid member (for example a blade) to wipe across a top surface of the dose cartridge. Optionally, the granulate substance is pulled into the dose chamber by applying vacuum before using the rigid member (for example a blade) to level it in position.

In some embodiments, the pallet is formed from the leveled granulate by compression by a pressing element. Compression is to a thickness which is, for example, in the range of 10-50% of the pre-compression thickness of the distributed granulate mass. Compression is, for example, to about 15%, 20%, 30%, 40%, or another larger, smaller, or intermediate value of the uncompressed thickness of the distributed granulate mass. In some embodiments, the granulate is compressed to a pallet of thickness within a range of between about 200-1500 µm, or thickness within another range having the same, larger, smaller and/or intermediate bounds.

Additionally or alternatively, pallet formation comprises placing a dose cartridge frame above a leveled granulate layer and using vacuum to pull up granulate material that is positioned immediately below the dose.

In some embodiments two or more leveling and/or pallet formation options are utilized for a single dose cartridge.

An aspect of some embodiments relates to positioning of a cartridge carrying a heat-vaporizing drug substance with integrated heating element within a clamping chamber which activates the heating element while confining the volatile components of the vaporizing drug substance to a substance delivery channel.

In some embodiments, the positioning is effected by movement of the cartridge along a track (for example, by a cartridge transport mechanism). In some embodiments, the chamber comprises at least one structure which encloses the cartridge on either side to seal it within a defined lumen, and/or makes electrical contact with a heating element of the cartridge. Optionally, electrical contact is on either side of the cartridge. Optionally, electrical contact is made on sides of the cartridge at points defined by the positioning of the cartridge relative to electrodes of an inhaler device. Optionally, contact pads extend from the heating element for the making of electrical contact therewith. Optionally the electrodes and dose cartridge are positioned such that the electrodes and the contacts on the cartridge are outside the sealed lumen while all vaporized material is confined to the inside of the lumen.

An aspect of some embodiments relates to a cartridge container for use with a substance vaporizer which is alternately:

attached to the cartridge container for receipt of a dose cartridge into the substance vaporizer; and detached from the cartridge container (magazine) for dose administration.

In some embodiments, the detachable drug substance vaporizer is used as part of an interlock mechanism for control of the dispensing of dose cartridges. For example, in some embodiments, the drug substance vaporizer is used as part of the activation of an interlock which prevents extraction of a new dose cartridge until a previously extracted cartridge is returned to a dispensing container.

Herein, the term "dose cartridge" refers to an assembly intended for a limited number of uses (usually one use, or uses confined within a brief session of inhalations), and comprising a material (for example, a botanical substance) carrying at least one drug substance, and optionally including additional elements for the transport, mechanical stabilization, and/or volatilization or vaporization (by heating, for example) of the drug substance. In some embodiments, a dose cartridge comprises drug substance material for deliver over no more than, for example, 1, 2, 3, or 4 inhalations. Material (optionally, a botanical substance) comprising a drug substance (and/or having a drug substance added thereto) and arranged within a dose cartridge is referred to herein as a "drug dose", "drug dose load" or "pallet"; "pallet" is used in particular to indicate a drug dose is arranged within or as the dose cartridge in flattened form, so as to be suitable for allowing air to be drawn through it for extraction of the drug substance. A pallet comprises, for example, a flattened expanse of porous material thin enough to permit airflow through and between the two largest faces. Herein, the term "drug substance" denotes one or more heat-vaporizing drug substances contained in and/or associated with a pallet for inhalation therefrom by a user.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Dose Cartridge with Integrated Heating Element

Figure 5A:
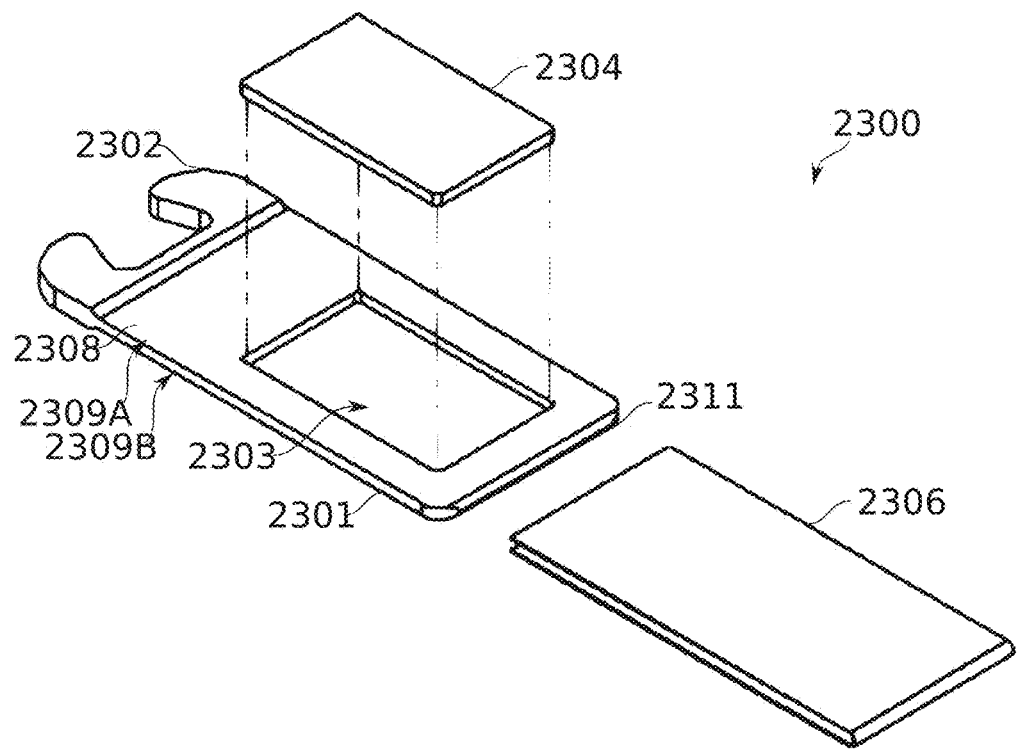
FIGS. 5A-5B are schematic views of a dose cartridge, disassembled and assembled, according to some embodiments.
Figure 5B:
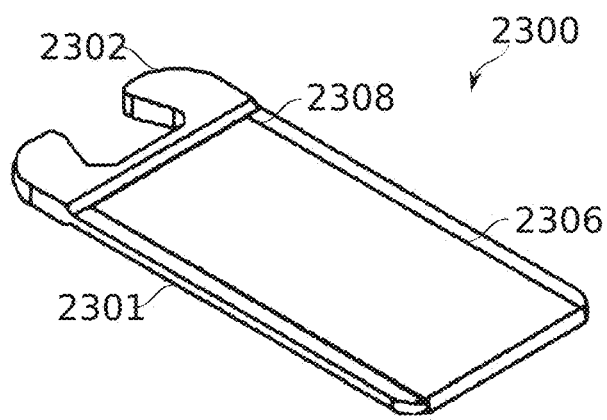
Figure 5C:
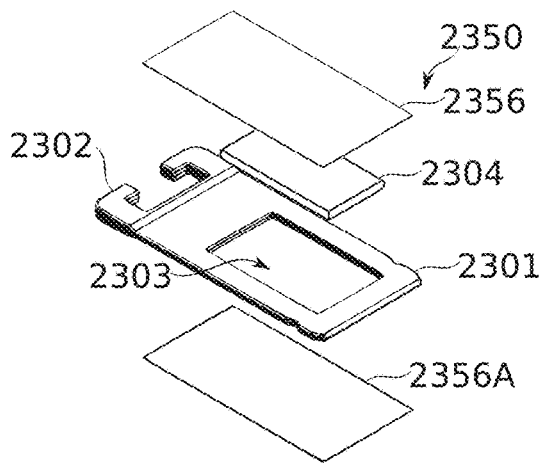
FIGS. 5C-5M schematically illustrate alternative constructions of dose cartridges, according to some embodiments.
Figure 5D:
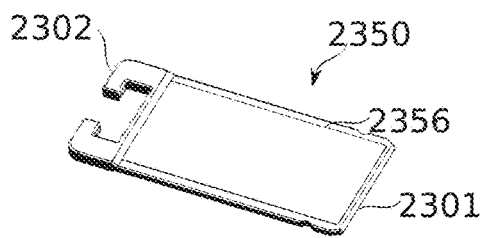
Figure 5E:
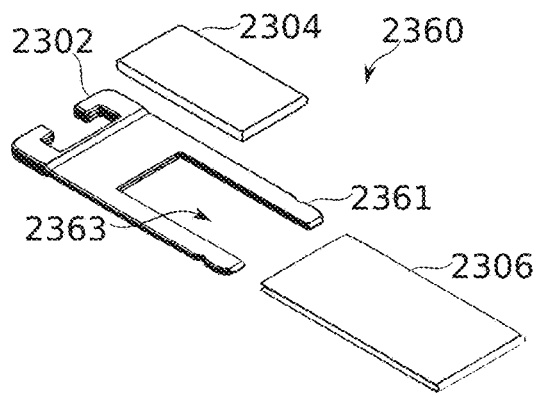
Figure 5F:
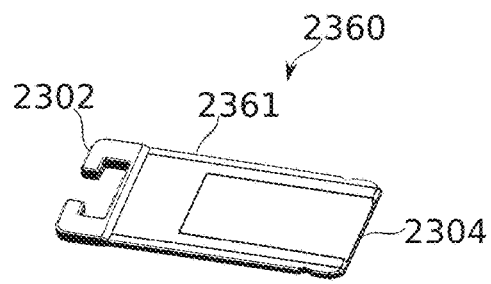

Reference is now made to FIGS. 5A-5B, which are schematic views of a dose cartridge 2300, disassembled (FIG. 5A) and assembled (FIG. 5B), according to some embodiments. Reference is also made to FIGS. 5C-5M, which schematically illustrate alternative constructions of dose cartridges 2350, 2360, 2370, 2380, 2390, and 2395, according to some embodiments. FIGS. 5C, 5E, 5G, 5J, and 5L show disassembled dose cartridges. FIGS. 5D, 5F, 5H, 5K, and 5M show assembled dose cartridges.

In some embodiments, drug doses comprising a drug substance are assembled upon and/or within a dose cartridge 2300. Optionally, the cartridge 2300 comprises:

a drug dose load 2304, optionally formed (for example, by flattening) for rapid vaporization;

mechanical support for the drug dose load 2304 (for example, support by enclosure within a housing 2301, which is optionally frame shaped);

an attachment element for facilitating transport of the cartridge 2300 (for example, latch mandibles 2302); and/or means for vaporizing the drug dose load 2304 (for example, an electrically resistive heating element 2306, optionally a mesh).

Different embodiment examples of the above-listed elements are described herein, as well as examples of embodiments of assembled dose cartridges which lack at least one of these elements. It is to be understood that the different element embodiments are optionally combined in embodiments of assembled dose cartridges in other combinations as well (for example, any heating element design provided with any frame design).

Optionally, the dose cartridge is disposable. Potential advantages of a disposable cartridge include: containment of drug dose and/or drug substance residue for disposal; close integration of dosage support and transport for reliable dosage transport within a vaporizer device; and/or reduced need to maintain and/or monitor portions of the vaporizer device (such as a vaporizing heating element) which are subject to conditions that could degrade performance over time.

Optionally, the dose cartridge is for use in a single inhalation. Potential advantages of a single-use cartridge include improving the precision and/or reliability in controlling the amount of drug substance vaporized under inhaler settings, as some relating to contamination and use damage are reduced.

In some embodiments, dose cartridge 2300 comprises a housing 2301 having a drug dose receiving chamber 2303. Optionally, the housing 2301 comprises a flattened and elongated strip; while the chamber 2303 comprises an aperture framed or partially frame by the strip. During preparation of the dose cartridge 2300 for dosing, a drug dose load 2304 is inserted into receiving chamber 2303. Optionally, the drug dose is formed—before or during insertion—such that it conforms to the flattened shape of the substance receiving chamber 2303. It is a potential advantage for the drug dose to be held in a flattened format (a "pallet", herein), since a greater surface area and/or a more uniform thickness potentially allow faster and/or more evenly distributed heating and/or airflow during dosage vaporization and delivery.

In some embodiments, the drug dose load or pallet dimensions are, for example, about 6×10 mm across the exposed surface area, and about 1 mm thick. Optionally, the thickness of the drug dose load is in the range of about 0.2-1.0 mm, or a greater, lesser, or intermediate thickness. Optionally, the face area of the drug dose load is in the range of about 20-100 mm$^2$; for example 20 mm$^2$, 40 mm$^2$, 50 mm$^2$, 60 mm$^2$, 80 mm$^2$, or another greater, lesser, or intermediate face area. The substance load is optionally formed into a square or substantially square pallet (for example, about 8×8×1 mm); optionally the pallet is oblong with a side ratio of, for example, 1:2, 1:3, 1:4, 1:10, or another larger, smaller, or intermediate ration of side lengths. Optionally, the pallet is, for example, about 30×2×1 mm in dimension. Corresponding dosing load by weight is about 15 mg in some embodiments. In some embodiments, the dosing load is selected from within a range of about 10-100 mg, or another range having the same, larger, smaller, and/or intermediate bounds.

It is a potential advantage to at least partially surround the drug dose load 2304 with a framing housing 2301 for greater mechanical stability. For example, botanical substances used to form a drug dose potentially comprise friable material, such that a drug dose load 2304 is liable to shed particles, particularly if bent and/or agitated. Enclosure within a cartridge frame allow the drug dose load 2304 to be moved within the system without applying stresses directly to the drug dose load 2304 itself and/or optionally renders it less sensitive to agitation. In some embodiments, the overall length and width of the cartridge is about 20×10 mm, or another larger, smaller, or intermediate size. During manufacture, a framing housing is a potential advantage for formation of a pallet of the correct size for fitted occlusion of a conduit through which air flows to pick up volatiles released during heating of the pallet.

Figure 5G:
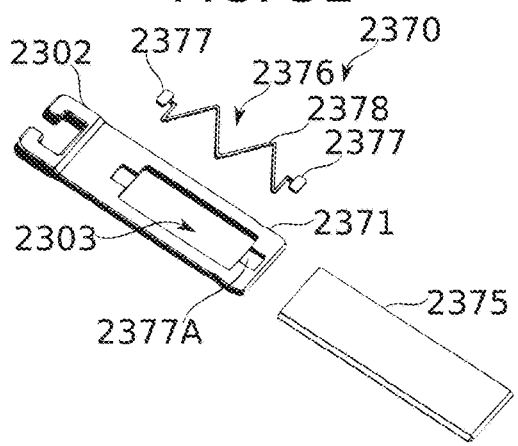

It is to be understood that completely surrounding the pallet is not required, in some embodiments, to achieve sufficient mechanical stability. For example, in some embodiments (FIGS. 5E-5F), a drug dose load 2304 is placed in an open-sided chamber 2363 defined by a "U" shaped frame portion 2361. Potentially, this allows packing the material of drug dose load 2304 into the cartridge 2360 from the open side of frame portion 2361. Potentially, the "U" shaped frame simplifies and/or speeds molding and/or release of the frame itself during manufacture. In some embodiments, the open side is closed off, for example, by a structure such as resistive heating element 2306, a permeable overlay 2375 (optionally a retaining mesh; FIG. 5G), or another structure.

In some embodiments, other support of a pallet is provided. A completely frameless example is shown, for example, in cartridge 2390A of FIG. 5L, where the whole extent of frame 2391A (optionally including even latch mandible 2392) is provided by the pallet material. In some embodiments, pallet material is sufficiently stable when prepared that no or relatively little additional mechanical support is required for use (for example, the pallet is compressed so that it remains intact during transport between a magazine and a clamping chamber). Optionally, at least a portion of the pallet material is mixed with a binder to add stability. Optionally, the pallet is a one piece pallet having sufficient stability, and which serves to hold a gel, fluid or powder comprising the heat-vaporizing drug substance.

In some embodiments, a one-piece pallet/frame is formed, optionally with a plurality of pallet materials, for example, a frame material for the region of frame 2391A (which may or may not comprise active substance), and a material containing drug substance for release in pallet region 2394A. Additionally or alternatively, the conditions of formation (for example, degree of compression packing) are different between the framing portion of the pallet, and the drug substance releasing portion of the pallet. In some embodiments, the drug substance releasing material covers, for example, about 60 mm$^2$ near the center of the pallet 2393. A drug substance releasing material is a drug substance-containing material, which releases that material, for example, in response to heating by a heating element 2306 located within and/or alongside it. In some embodiments, a heating element 2306 also provides mechanical support. Optionally, the pallet/frame assembly 2393 in turn provides electrical insulation between parts of the heating element 2306. Attachment between heating element 2306 and pallet 2393 is, for example, by using any method known in the art that would remain stable during use, including, for example, one or more of welding, glue, cold press, hot press and/or pins.

In some embodiments (for example, cartridge 2395 of FIG. 5M), a pallet 2399 is provided with perforations 2398 which increase its permeability to flow. This is of particular potential benefit for frameless or nearly frameless cartridge embodiments. Pallet 2399 of dose cartridge 2395, for example, is bounded only by latch mandible 2396 (which is optionally formed as an integral part of the pallet) and (transparently drawn) "U" shaped heating element 2306. Potentially, packing pallet material with sufficient density to achieve mechanical self-stability reduces the airflow permeability of the resulting pallet, thus interfering with drug volatilization. Perforations 2398 are provided, for example, by introducing gaps with the tooling (a mold, for example) used in packing the bioactive material, by perforating the pallet after formation, or by another method.

In some embodiments, (cartridge 2390 of FIGS. 5J-5K), the mandibles 2391 are provided as a separate part (for example, manufactured of polymer or metal), attached to a pallet 2394 of material (for example, one or more botanical substances) comprising the drug substance to be released. In some embodiments, a heating element 2306 or another wrapping structure provides additional mechanical support. Optionally, attachment of pallet 2394 to mandibles 2391 comprises use of an adhesive. Optionally, attachment comprises mechanical interconnection; for example, one of the mandibles 2391 and pallet 2394 is formed with a tab, and the other with a slot, and/or the mandibles 2391 are provided with protrusions (for example, a comb of spikes) around which the pallet 2394 is formed.

In some embodiments (e.g. the cross section of dose cartridge 2380 shown in FIG. 5I), a heating element 2386 which wraps a pallet 2304 is welded at a join 2381 where two sides of the heating element come together. Potentially, this provides an advantage for providing additional mechanical stability to a pallet 2304 (and particularly, for one of the frameless or partially frameless embodiments). Since the weld 2381 changes the electrically conductive topology of the heating element 2386, electrodes 2331 are optionally placed at in electrical contact with the heating element 2386 on its opposite ends (optionally, but not necessarily, in contact with the weld region 2381 itself).

In some embodiments, vaporization of a portion (for example, a volatile portion) of the drug dose comprises heating by an electrically resistive heating element (mesh, or other form of resistive heating element) 2306. The resistive heating element optionally comprises a material which displays substantial electrically resistive heating; for example, nichrome (typical resistivity of about 1-1.5 μΩ·m), FeCrAl (typical resistivity of about 1.45 μΩ·m), stainless steel (typical resistivity of about 10-100 μΩ·m), tungsten (typical resistivity of about 52.8 nΩ·m), and/or cupronickel (typical resistivity of about 19-50 μΩ·m). According to the choice of metal, parameters such as heating element length and width, metal thickness, aperture size and/or aperture pattern are adjusted to comprise a total resistance across the resistive heating element which is, for example, in the range from about 0.05-1Ω, 0.5-2Ω, 0.1-3Ω, 2-4Ω, or within another range having the same, higher, lower, and/or intermediate bounds.

Optionally, during assembly, the resistive heating element 2306 is attached to the housing 2301, in a position overlying the drug dose load 2304 on one or more sides. For example, the resistive heating element 2306 extends from a dorsal surface 2309A to fold around housing end 2311, and extend back along ventral surface 2309B. Optionally, resistive heating element 2306 extends around chamber 2303 such that a drug dose load 2304 contained within chamber 2303 is enclosed by the heating element 2306. In some embodiments, the resistive heating element 2306 comprises a plurality of separate panels, for example, panels 2356 and 2356A of FIGS. 5C-5D, one on each side of the cartridge 2350. Optionally, the panels are electrically connected, one to the other. Alternatively, each receives separate electrical connections. A potential advantage of two-sided enclosure of the drug dose load 2304 (used in some embodiments) is increased speed and/or uniformity of volatilization upon application of a current to the heating element 2306. In some embodiments, only one panel 2356 of the enclosure is an electrically resistive element, and the other panel 2356A is optionally a mesh or other air-permeable structure (for example, a porous structure) which provides mechanical support.

In some embodiments, electrically resistive heating elements 2356, 2356A are operated simultaneously. In some embodiments, the resistive heating elements are operated separately. This is a potential advantage, for example, to allow separate control and/or release of two different substances, and/or of a single substance in two sequential dosing sequences. For example, a first heating element (panel, for example) is operated with sufficient energy to vaporize drug substance directly underneath it, but for a sufficiently short time or in such a heating pattern that the heat does not reach all the way through the pallet. At some offset in time (optionally overlapping or entirely separate from the first heating), a second heating element is operated. Potentially, this is an advantage when two substances having different volatilization properties as a function of time or temperature are to be released (for example, from two different pallet materials). Optionally, the two heating profiles are adjusted to result in simultaneous vaporization. Additionally or alternatively, vaporization of two substances is deliberately offset in time. For example, material comprising a flavoring or masking agent is placed in the pallet near a heating element where it is vaporized first, and a second material vaporized shortly thereafter (or the reverse). This is a potential advantage, for example, to mask potentially unpleasant tastes, to signal a user as to a status of vaporization in process, and/or to otherwise modify the sensory experience of inhalation. Optionally, each electrode heats across a whole side of the pallet. Alternatively, each heating element is formed so that vaporization heating occurs only across a portion of the pallet, optionally in a different portion for each electrode. In some embodiments, one heating element is used to "prewarm" a substance to a threshold below active substance release, and a second heating element is activated to achieve release itself. Potentially, prewarming followed by release heating shortens a period of substance release and/or increases a concentration upon release. Potentially, this helps to increase the amount of substance reaching the lungs, and/or to target release to a narrower selected respiratory depth.

Figure 5H:
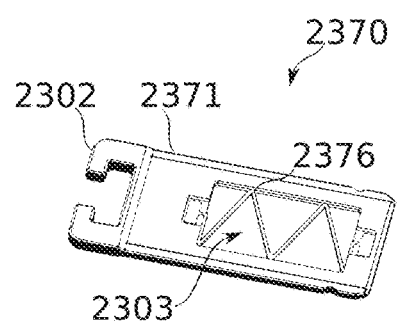
Figure 5I:
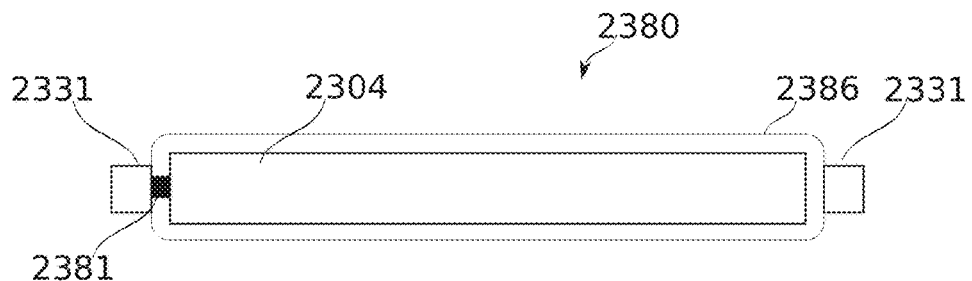
Figure 5J:
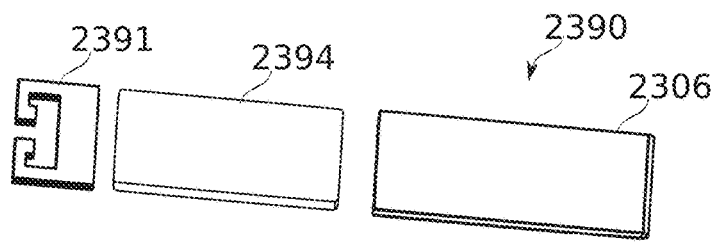
Figure 5K:
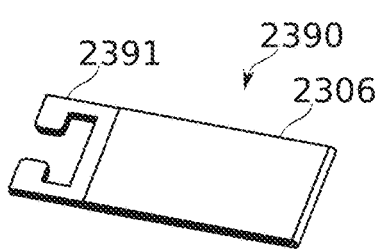
Figure 5L:
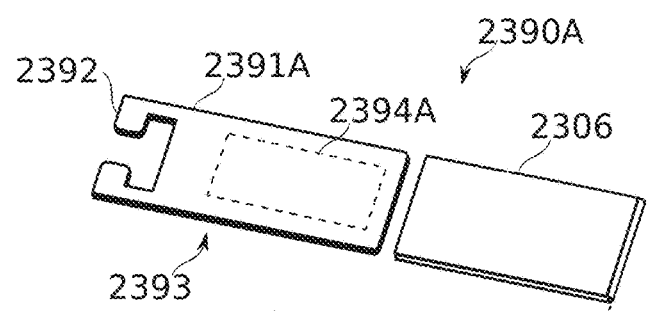
Figure 5M:
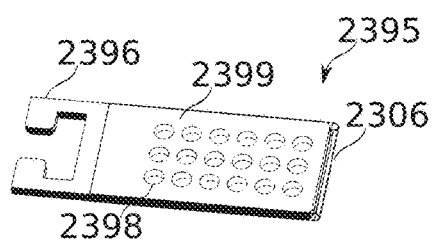
Figure 6A:
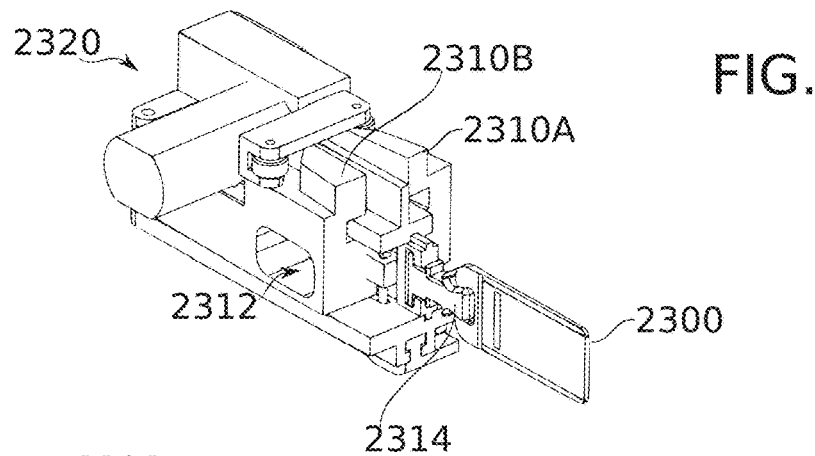
FIGS. 6A-6E schematically illustrate a carousel-type dose delivery system for use with an inhaler device, according to some embodiments.
Figure 6B:
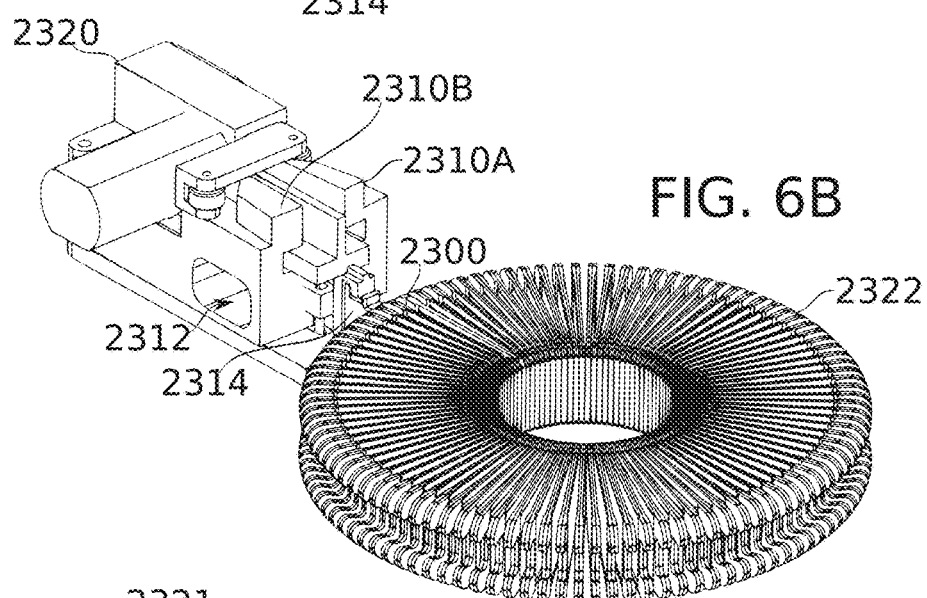
Figure 6C:
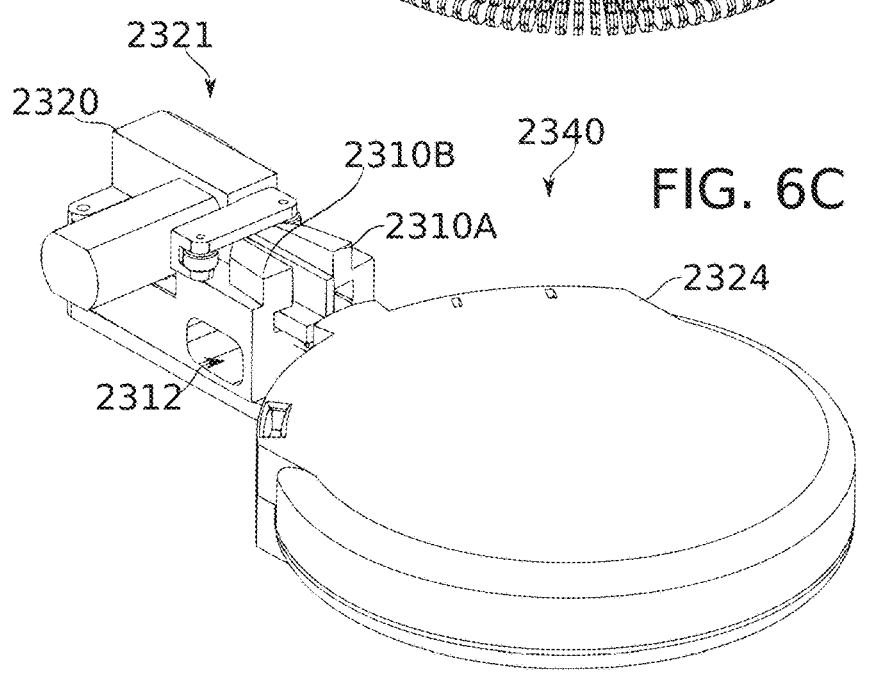
Figure 6D:
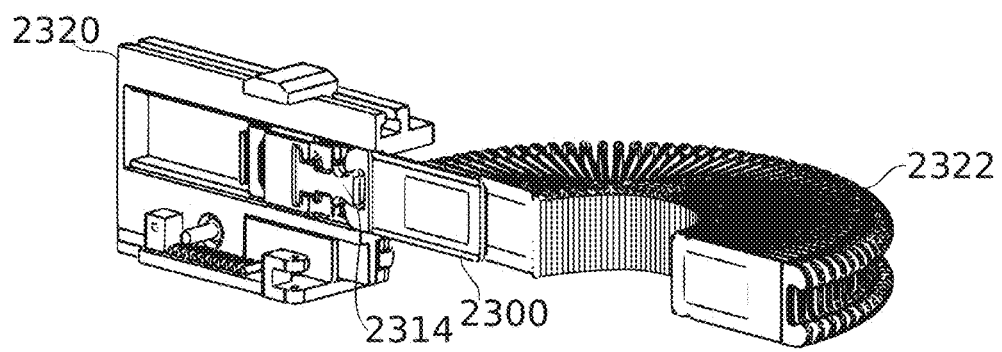
Figure 6E:
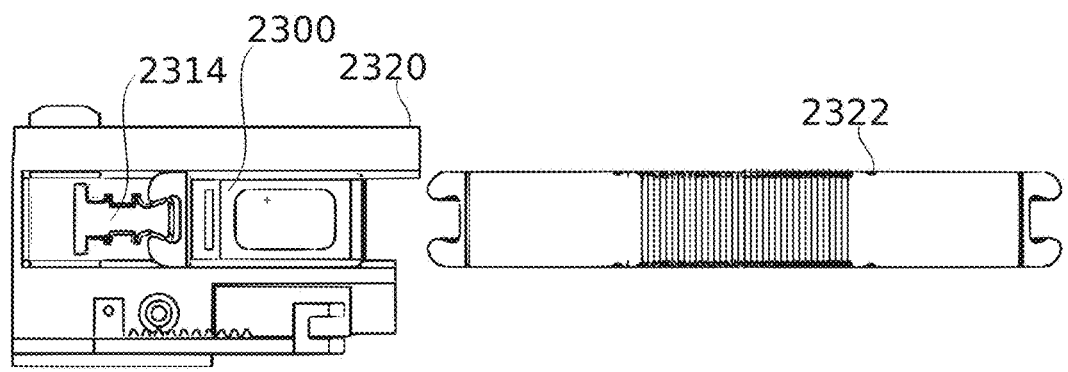

In some embodiments, at least one heating element 2306 is embedded wholly or partially within a drug dose load (pallet) 2304 (also shown, for example, in FIGS. 5G-5H). Optionally, a heating element 2306 is embedded partially or wholly within the frame of a housing 2301. For example, the housing 2301 is originally molded with the heating element in place, and/or the heating element 2306 is pressed into place under high temperature at another stage of manufacturing. Optionally a plurality of heating elements 2306 are embedded wholly or partially within a drug dose load (pallet) 2304, with electrical contacts optionally arranged to allow separate or simultaneous operation.

In some embodiments, resistive heating element 2306 and/or permeable overlay 2375 comprises a ratio of open (aperture) to closed (mesh or other material) surface area of between about 1:1 (50%) and 1:3 (33%). In some embodiments, the ratio is in the range of about 10%-20%, about 20%-40%, about 30%-50%, about 40%-70%, about 60%-80%, about 70%-90%, or another range of ratios having the same, larger, smaller, and/or intermediate bounds. In some embodiments, the apertures of the mesh are in the range of about 25 μm, 32 μm, 50 μm, 75 μm, 100 μm, 200 μm, 300-750 μm, 700-1200 μm, or another larger, smaller, or intermediate range. Optionally, at least two apertures have different size and/or shape.

FIGS. 5G-5H show another embodiment of a cartridge 2370 comprising an embedded heating element 2376 in a frame 2371. In some embodiments, heating element 2376 comprises a heating section 2378 arranged between a plurality of electrode pads 2377. In the assembled dose cartridge, heating section 2378 extends across or within chamber 2303 and across or through a pallet 2304. For example, pallet 2304 is optionally formed by pressing loose material into place around the heating element 2376, embedding it. Optionally, frame 2371 comprises one or more recesses 2377A, which receive electrode pads 2377. In some embodiments, additional mechanical support for the pallet is provided by a permeable overlay 2375, extending over at least one side of the cartridge frame 2371. Overlay 2375 optionally comprises a polymer mesh or other structure allowing gas flow.

In some embodiments, the heating section 2378 of heating element 2376 is formed as a wire which crosses chamber 2303 one or more times in connecting to electrode pads 2377. In some embodiments, heating section 2378 comprises a mesh, ribbon, or other shape. In some embodiments, heating section 2378 is divided into a plurality of separate parts (branches, layers, or other divisions). In some embodiments, the heating section 2378 extends nearby (for example, within 1 mm, within 2 mm, or within another larger or smaller distance) substantially all parts of the pallet containing the drug substance to be released. This is a potential advantage for obtaining more rapid and/or uniform substance release upon heating.

It is to be understood that although electrode contacts 2377 are electrically separated from one another except as joined by the heating section 2378, they need not be placed physically distant from one another, depending, for example, on the course(s) run by the heating section 2378 itself. Optionally, the electrode contacts are placed on the same or on different sides of chamber 2303, for example.

In some embodiments, resistive heating element 2306 comprises an etched resistive foil (for example a foil etched into a continuous ribbon or other shape, and backed by a polymer such as polyimide and/or silicone rubber). Optionally a backed resistive foil is perforated through the backing to allow airflow during volatilization of the drug dose. In some embodiments, a fuse is added to the resistive foil, for example as an added component, and/or as a region of ribbon manufactured deliberately thin, so as to provide a method of destroying the heating element after use (by sending an appropriately high current through the heating element for a sufficient period of time).

In some embodiments, resistive heating element 2306 is secured to the cartridge housing 2301 by pressing the heating element onto the housing (for example, at housing region 2308) using a temperature high enough for the housing to melt and/or soften such that the heating element becomes embedded in the material of the housing. This is particularly appropriate, for example, for use with a housing comprising a thermoplastic. Alternatively (for example, if the housing comprises a thermoset polymer), cold press joining is used. Additionally or alternatively, the heating element is secured by ultrasonic welding, crimping, gluing, or another method of joining.

In some embodiments, the housing comprises an inert, thermally resistant material. In some embodiments, the housing material used comprises, for example, a liquid crystal polymer (LCP), polyether ether ketone (PEEK), Ultem, Teflon, Torlon, Amodel, Ryton, Forton, Xydear, Radel, Udel, polypropylene, Propylux, polysulfone, polyether sulfone, acrylic, ABS, nylon, PLA, polybenzimadazole, polycarbonate, polyetherimide, polyethylene, polyphenylene oxide, polyphenylene sulfide, polystyrene, polyvinyl chloride, another thermoplastic, and/or another polymer material. In some embodiments, the housing comprises a non-conductive and/or semiconductive material. In some embodiment, the housing comprises a conductive material (for example, aluminum), optionally insulated electrically from the resistive heating element, for example by an insulating layer such as an anodized coating.

A potential advantage of LCP and/or PEEK is good resistance to temperature higher than a temperature needed to vaporize a substance held in the cartridge. In some embodiments, bonding of heating element and housing occurs at a temperature of about 280° C. (or another temperature high enough to melt and/or soften LCP or PEEK). LCP and PEEK provide the potential advantage of good thermal stability at lower temperatures, for example, at a vaporization temperature of about 230° C.

In some embodiments, a conductive or semi-conductive housing material is used, optionally provided with a non-conductive separator. For example, the housing material comprises anodized aluminum.

A potential advantage of providing a heating element such as an electrically resistive heating element 2306 for each individual dose cartridge is to provide uniformity of performance between uses. Potentially, a portion of the heated compounds with which a heating element comes into contact remain stuck to the heating element after cool down. This buildup has the potential to affect vaporization performance. Remote heating (by radiation and/or indirect conductance, for example) potentially produces a system having relatively high thermal inertia (needing greater heating power) compared to direct conductive heating by a contact electrode; the problem of contact electrode contamination is removed by designing it for single use. A lowered requirement for heating potentially increases safety and/or device longevity. Potentially, a lowered requirement for heating also lowers demands on power delivery, allowing embodiments with increased portability, greater charge life, and/or lowered expense (for example, for systems having battery-powered heating elements).

In some embodiments, a cartridge 2300 comprises a locking member for use in cartridge transport. The locking member comprises, for example, a latch mandible 2302. The locking allows engagement by one or more matching members of a vaporizer device transport mechanism, for securing and/or movement of the cartridge. Cartridge movement and/or securing against unwanted movement may occur during the cartridge life cycle, for example: when the cartridge is placed into a queue of cartridges comprising a plurality of cartridges arranged for use, when the cartridge is advanced in the queue, when a cartridge is selected for use, when a cartridge is moved into position for use, when a cartridge is actually used, and/or when a cartridge is discarded, or, alternatively, moved to a "used" position in the cartridge queue.

In some embodiments, a dose cartridge 2300 comprises a button cartridge, wherein the drug dose is substantially encapsulated by a porous, flattened capsule which optionally comprises the material of the heating element surrounding or nearly surrounding the drug dose. The porous capsule is, for example, round, square, rectangular, oval, or another shape. Optionally, transport of a button cartridge comprises, for example, pressing, pulling, and/or clamping the surfaces of the capsule, and/or operation of magnets (where the button cartridge comprises magnetically susceptible material). In some embodiments, at least one portion of a dose cartridge 2300 (a button cartridge, or any other dose cartridge) is sufficiently thick alongside one or more edges of the drug dose pallet itself to avoid or reduce wastage and/or uneven drug substance release from the volume of the pallet. For example, a side support member of the dose cartridge is large enough to allow a stable hold, while substantially the entire drug dose pallet is heated to release drug substance which can freely diffuse into a stream of airflow.

In some embodiments, a dose cartridge 2300 comprises a central support member surrounded by drug dose substance, which bridges between two faces of the drug dose to interconnect a plurality of air-porous pallet face supports. For example, a dose cartridge comprises a spindle or reel frame shape, with the substance of the drug dose pallet packed around the core of the spindle. Optionally, transport and/or holding of the dose cartridge comprises manipulation of the core of the spindle, which is optionally hollow, and the hollow is optionally open on at least one face of the dose cartridge.

Granulation of Botanical Substance

Figure 3:
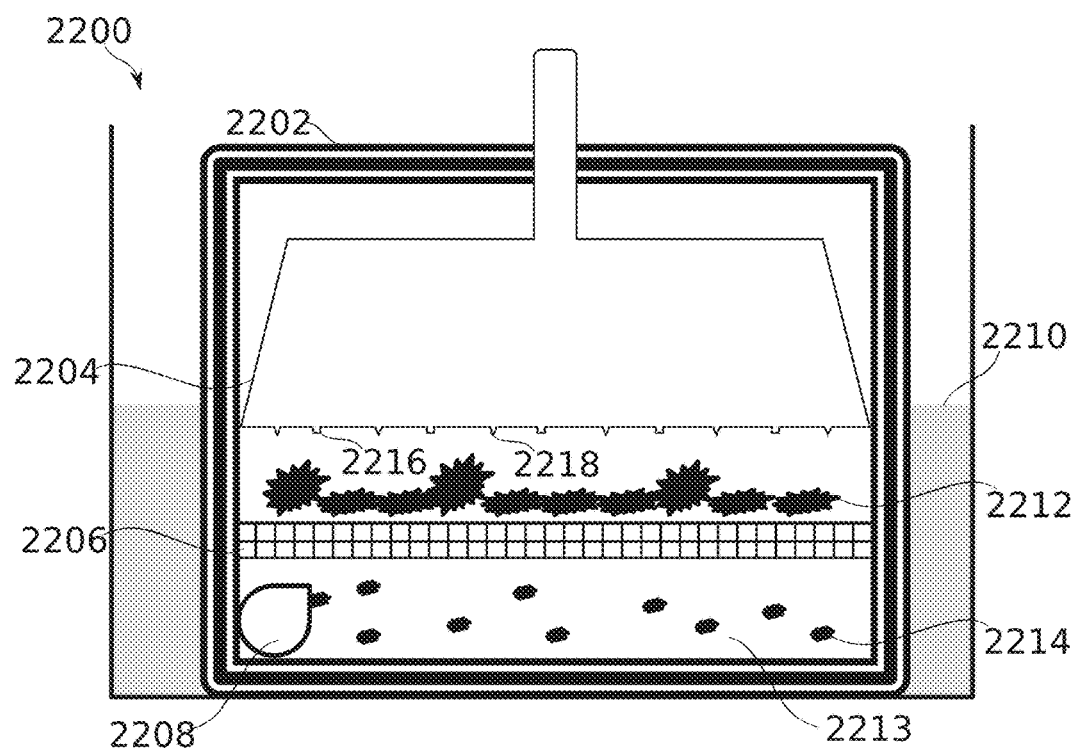
FIG. 3 is a schematic view of a botanical substance grinding apparatus, according to some embodiments.

Reference is now made to FIG. 1, which is a schematic flowchart of a method of preparing a granulated botanical substance for use in dose packaging with an inhaler device, according to some embodiments. Reference is also now made to FIG. 3, which is a schematic view of a botanical substance grinding apparatus 2200, according to some embodiments. Reference is also made to FIG. 4, which is a schematic view of the grinding plate 2220 of a botanical substance grinding head 2204, according to some embodiments.

In some embodiments, formation of a drug dose load 2304 comprises processing through a granulated intermediate form 2214 of an organic substance (for example, a botanical substance 2212). Granulation optionally allows control of drug dose load 2304 shape, structure, and/or density. A potential advantage of granulation is to increase the grain surface area exposed to gas (for example, heated gas) passing through a permeable drug dose load 2304. Potentially, granulation allows increased homogenization of the drug dose load, for increased reproducibility of dosage amount.

At block 2002, in some embodiments, the flowchart begins, and a botanical substance for use in formulating a dosage is received. In some embodiments, the botanical substance comprises *cannabis*, optionally *cannabis* flowers in particular. In some embodiments, a botanical substance received for use in formulating dosage comprises any whole or portion of a plant, including for example one or more of: *Cannabis sativa, Cannabis indica, Cannabis ruderalis, Acacia* spp., *Amanita muscaria,* Yage, *Atropa belladonna, Areca catechu, Brugmansia* spp., *Brunfelsia latifolia, Desmanthus illinoensis, Banisteriopsis caapi, Trichocereus* spp., *Theobroma cacao, Capsicum* spp., *Cestrum* spp., *Erythroxylum coca, Solenostemon scutellarioides, Arundo donax, Coffea arabica, Datura* spp., *Desfontainia* spp., *Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea* spp., *Nelumbo* spp., *Sophora secundiflora, Mucuna pruriens, Mandragora officinarum, Mimosa tenuiflora, Ipomoea violacea, Psilocybe* spp., *Panaeolus* spp., *Myristica fragrans, Turbina corymbosa, Passiflora incarnata, Lophophora williamsii, Phalaris* spp., *Duboisia hopwoodii, Papaver somniferum, Psychotria viridis,* spp., *Salvia divinorum, Combretum quadrangulare, Trichocereus pachanoi, Heimia salicifolia, Stipa robusta, Solandra* spp., *Hypericum perforatum, Peganum harmala, Tabernaemontana* spp., *Camellia sinensis, Nicotiana tabacum, Nicotiana rustica, Virola theidora, Voacanga africana, Lactuca virosa, Artemisia absinthium, Ilex paraguariensis, Anadenanthera* spp., *Corynanthe yohimbe, Calea zacatechichi, Coffea* spp. (*Rubiaceae*), *Sapindaceae* spp., *Camellia* spp., *Malvaceae* spp., *Aquifoliaceae* spp., *Hoodia* spp. *Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis,* Tobacco, Aloe Vera, Angelica, Anise, Ayahuasca (*Banisteriopsis caapi*), Barberry, Black Horehound, Blue Lotus, Burdock, Camomille/Chamomile, Caraway, Cat's Claw, Clove, Comfrey, Corn Silk, Couch Grass, Damiana, Damiana, Dandelion, Ephedra, Eucalyptus, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, *Sida Cordifolia*, Sinicuichi (Mayan Sun Opener), Spearmint, Sweet Flag, Syrian Rue (*Peganum harmala*), Thyme, Turmeric, Valerian, Wild Yam, Wormwood, Yarrow, Yerba Mate, and/or Yohimbe. The dosing botanical substance optionally includes any combination of plant material from this list, and/or other plant material.

Grinding of the botanical substance is described with respect to the use of a grinder 2200, for purposes of illustration. It is to be understood that in some embodiments, another grinders capable of producing particles of sufficiently small size and uniformity for forming into a drug dose load are used. Optionally, the grinder is capable of producing the particles without significantly damaging the macroscopic plant structure of the botanical substance, for example without bursting and/or breaking the trichomes of a *cannabis* plant.

At block 2004, in some embodiments, the botanical substance 2212 is placed in a sieving chamber. The sieving chamber comprises a mesh or other perforated surface 2206, the perforations being, for example, about 500 µm in pore size. Optionally, the pore size is, for example, about 250-400 µm, 350-600 µm, 500-700 µm, 650-900 µm, 800-1000 µm, or another range of pore sizes having the same, larger, smaller, and/or intermediate bounds.

At blocks 2006, and 2008 in some embodiments, the sieve is placed in a grinder body 2202, optionally together with a moisture absorption substance 2208. Moisture absorption substance 2208 helps to keep control the moisture content of the granules 2214, for example, to obtain a consistent range of granulated material characteristics including self-adhesion, and relative weight-percent dose concentration. Potentially, the moisture absorption substance 2208 helps to prevent free-frost formation during the cryogenic stages of the grinding process.

At block 2010, in some embodiments, the grinder 2200 is cooled. Optionally, the cooling is using a cryogenic fluid 2210 to a temperature in the range, for example, of −50° C. to −180°. Optionally, the cryogenic fluid 2210 is liquid nitrogen, or another cryogenic fluid appropriate to the target temperature range.

Figure 4:
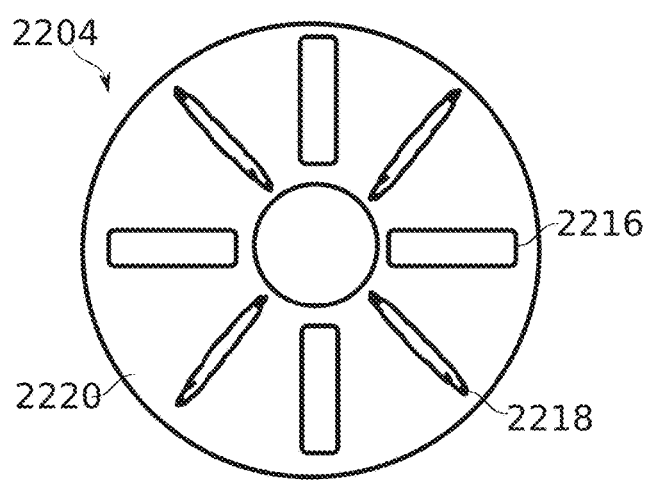
FIG. 4 is a schematic view of the grinding plate of a botanical substance grinding head, according to some embodiments.

At block 2012, in some embodiments, a grinding head 2204 is lowered to the level of the botanical substance while spinning, and gradually lowered further as particles are further ground. An example of a grinding head grinding plate 2220 is shown in FIG. 4, comprising rigid protrusions 2216 (which act to break up the frozen botanical substance when they press against it). Optionally, fine brushes 2218 act to spread particles of ground material over the plate, such that particles which have been ground to a sufficient degree of fineness fall through the sieving pores into a receiving chamber 2213.

At blocks 2014 and 2016, in some embodiments, the grinder is brought back to ambient temperature, unsealed, and the sieved granulate removed from the receiving chamber 2213. The granulate is homogenized, for example, by use of a V-mixer, circular mixer, or other homogenizing process.

Packaging of a Botanical Substance to a Dose Cartridge

Figure 2:
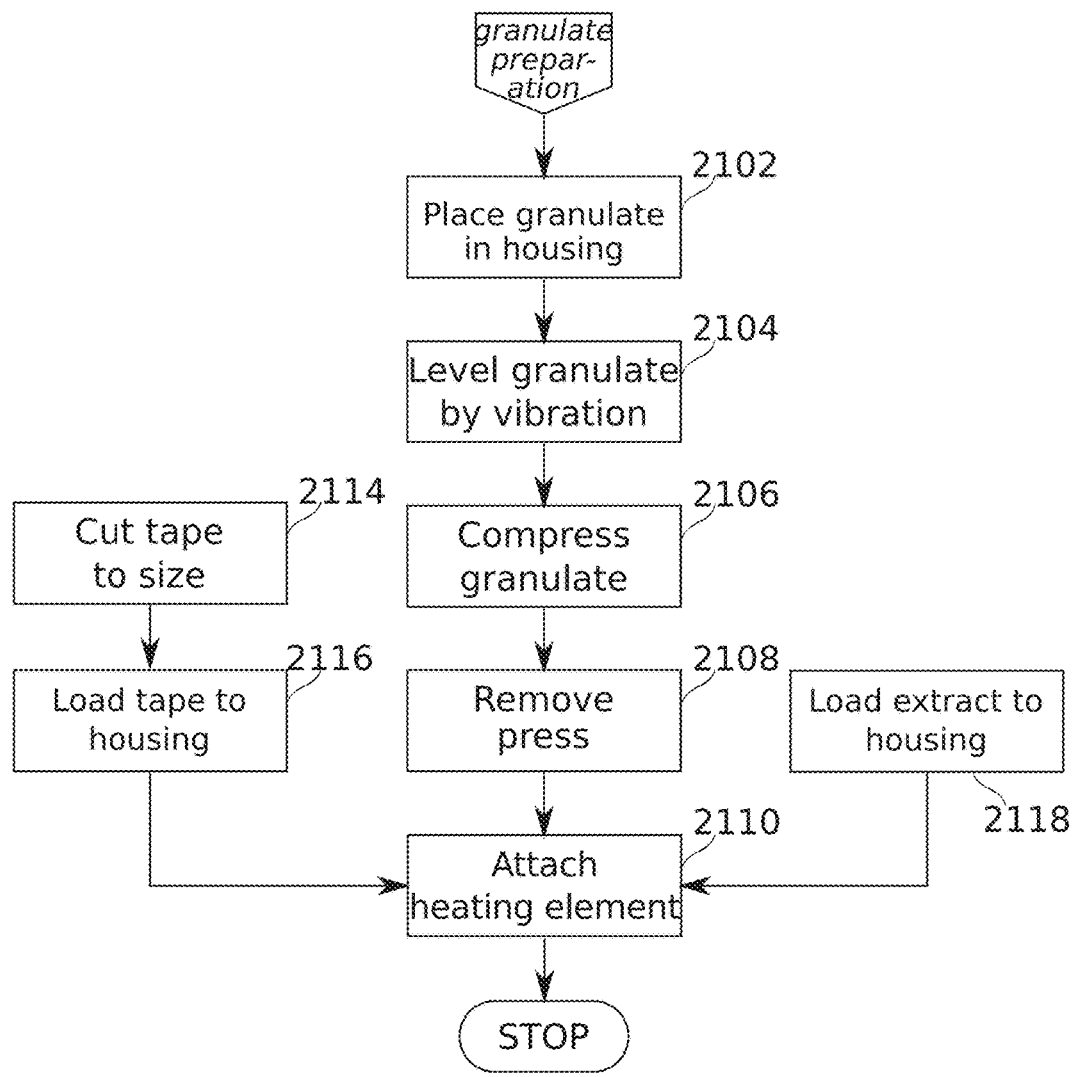
FIG. 2 is a schematic flowchart of a method of packaging a botanical substance to a dose cartridge for use with an inhaler device, according to some embodiments.

Reference is now made to FIG. 2, which is a schematic flowchart of a method of packaging a botanical substance to a dose cartridge for use with an inhaler device, according to some embodiments.

In some embodiments, material for forming a drug dose (for example, granulated material, as described in relation to FIG. 1) is incorporated into a dose cartridge 2300 by a process of pressing a metered amount of the material into a receiving chamber 2303 in the cartridge. Optionally, the pressing is to a degree which provides a chosen degree of thinness (thinner packages potentially heat more quickly and/or evenly), and/or a chosen degree of density (a package should not be too dense to allow the passage of airflow during vaporization).

At block 2102, in some embodiments, a first branch of the flowchart begins for the cartridge packages of botanical granulate. In some embodiments, the humidity and temperature of the packaging area are controlled, for example, to a temperature of 20° C. and a humidity of 30%. It should be understood that other environmental conditions are used in some embodiments (for example, the temperature can potentially be within about ±5° C. of 20° C.; the humidity can be within about ±10% of 30%). The variables of temperature and humidity, as selected, may be set to consistent levels in order to maintain consistent dosing. Also, conditions selected should be such that the botanical granulate neither becomes too dry to pack well, nor too wet to distribute evenly.

A measured amount of botanical granulate is placed in an open receiving chamber 2303 of a dose cartridge housing 2301. Optionally, one side of receiving chamber 2303 is closed by an electrically resistive heating element 2306 which is optionally a mesh, or another heating element which is perforated to permit the passage of air through the granulate, while retaining the granulate in place. Alternatively, the receiving chamber 2303 is placed against a firm flat surface from which the granulate is easily removed (for example, a relatively low friction polymer surface such as PTFE). Optionally, receiving chamber 2303 comprises a thin, heat-conductive bottom wall which is perforated to permit the passage of air through the granulate, while retaining the granulate in place.

Optionally, receiving chamber 2303 comprises a reticular formation (a net, mesh, or other structure), which serves as an anchor for material during pressing (for example, at block 2106). In some embodiments, a reticular formation or a permeable retaining element which is optionally not itself a heating element is provided on the exterior of the dose cartridge, serving to provide mechanical support for a pallet in the receiving chamber 2303, while also permitting the passage of air.

The amount of measured granulate is optionally chosen according to the potency, concentration, and/or volatility of the vaporizing fraction. When *cannabis* granulate is used, for example, the measured amount is optionally 15 mg, or another value in the range of 10-20 mg. Choice of amount optionally depends, for example, on plant variety, growing conditions, and/or assay results of a botanical substance available for packaging. In some embodiments, the measured amount is within the range, for example, of 1-20 mg, 10-40 mg, 25-75 mg, 50-100 mg, or within another range of amounts having the same, intermediate, larger, or smaller bounds. In some embodiments, for example, if the required dosage is too small to fill the substance receiving chamber, a filler substance is optionally added; for example, a portion of an inert (lacking volatile drug activity) botanical substance. Optionally, the filler is uniformly mixed with the required dosage.

At block 2104, in some embodiments, the granulate is distributed within the receiving chamber 2303. In some embodiments, distribution comprises leveling the housing 2301 (placing it horizontally flat), and shaking the housing with the granulate inside vertically (for example, by vibrating the cartridge 2300 and/or the surface that the cartridge housing 2301 rests on), until a leveled plain of granulated substance is formed within the chamber 2303. In some embodiments, the vibrating is with an amplitude in the range of about 0.1-1.2 mm; for example 0.5 mm. The frequency of vibration is, for example, in the range of about 20-300 Hz (such as 30 Hz, 45 Hz, 60 Hz, 75 Hz, or another higher, lower, or intermediate frequency). Duration of shaking is, for example, chosen from within the range of 100-1100 msec (such as about 300 msec, 400 msec, 500 msec, 800 msec, or another longer, shorter, or intermediate time). Optionally, the chamber is secured before vibration, to prevent granulate from escaping the chamber from underneath.

At block 2106, in some embodiments, granulate is compressed by the use of a press. Optionally, the press lowers vertically down upon the distributed granulate, forming it into a small pallet 2304 of compressed granules. Compression is to a thickness which is, for example, in the range of 10-50% of the pre-compression thickness of the distributed granulate mass. Compression is, for example, to about 15%, 20%, 30%, 40%, or another larger, smaller, or intermediate value of the uncompressed thickness of the distributed granulate mass. In some embodiments, the granulate is compressed to a pallet of thickness within a range of between about 200-1500 µm, or thickness within another range having the same, larger, smaller and/or intermediate bounds.

At block 2108, in some embodiments, the press is removed. In some embodiments, the press is removed by sliding horizontally across the surface of the cartridge housing 2301. Potentially, this allows granulate residue which may stick to the press tool to be scraped off at the edge of the receiving chamber 2303. Optionally, granulate which has been compressed into the chamber is fixed thereby, and remains in place during additional handling to finish the cartridge preparation.

Other methods of filling the drug dose receiving chamber are also contemplated as separate embodiments as will be apparent below.

For example, at block 2114, in some embodiments, an alternative branch of the flowchart begins. As an alternative to the formation by granulate pressing of drug dose load 2304 for a cartridge 2304, a portion of a botanical substance tape is trimmed to the size of a substance receiving chamber 2303 of a dose cartridge housing 2300. In some embodiments, the botanical substance tape is formed, for example as described in International Patent Application Publication No. 2012/085919. At block 2116, in some embodiments, the trimmed tape portion is inserted to the substance receiving chamber 2303.

Also for example, at block 2118, in some embodiments, another alternative branch of the flowchart begins. Optionally, a material containing a drug substance from which a drug dose is formed is available as fluid and/or gelatinous extract, fine suspension, and/or solution. The drug dose receiving chamber then optionally comprises an air-permeable portion (for example, foam, sponge, felt or other fiber matrix, and/or another porous structure) which absorbs the drug substance containing material to fix it into place.

At block 2110, in some embodiments, any one of the three branches continues. Resistive heating element 2306 (a mesh, for example, or another heating element such as an etched foil) is attached to the cartridge housing 2301, for example by pressing against the housing and heating until the two parts are fused by softening and/or melting of the housing material. Attachment is optionally on one or both sides of the substance receiving chamber 2303. In some embodiments, a heating element in a "U" shape wraps around the cartridge housing 2301 to enclose the chamber 2303 on two sides, for example, within the hollow of the "U".

Dose Cartridge Carousel and Vaporizing Device

Reference is now made to FIGS. 6A-6E, which schematically illustrate a carousel-type dose delivery system 2340 for use with an inhaler device, according to some embodiments.

In some embodiments, the dose delivery system 2340 comprises a carousel 2322 holding a plurality of dose cartridges 2300 encased by an enclosure 2324, and an inhaler device 2321 comprising a dose puller 2314 and a clamping chamber 2320. Carousel enclosure 2324 and the inhaler device 2321 are attached to one another; the carousel 2322 revolves to present cartridges to the inhaler device 2321 in the order of their positions within the carousel, or in another order, as selected by operation of the carousel 2322. Optionally, the carousel enclosure 2324 (and its contents) are exchangeable for a new enclosure assembly, for example when dosages are exhausted, and/or to change the dosing composition. The number of dosage cartridges carried by an enclosure is, for example, about 100. Optionally, the number of cartridges is another number within the range of 10-200 (for example, 10, 40, 80, 120, 180, or 200), or another larger or smaller number. In some embodiments, carousel diameter is, for example, within the range of about 7-10 cm, or another larger or smaller diameter, according, for example, to the number and size of cartridges to be accommodated. Optionally, carousel 2322 comprises identical doses or a plurality of different doses (for example, different amounts, concentrations, and/or substance compositions). It is to be understood that a carousel is not the only form of cartridge storage device (magazine) which is usable with dose cartridges. For example, the dose cartridges can be stored within a linear-type magazine storage system (for example, as described in relation to FIGS. 11A-11C). A potential advantage of a carousel over a linear-type magazine is rotationally selectable access during loading and/or unloading to dosing positions; for example, to effect a dosing regimen (namely, to provide the user with a defined sequence of inhalations from dose cartridges each having a different substance and/or a different amount of a substance and/or different substance ratios) and/or to adjust a dosing regimen after the magazine was already loaded with dose cartridges. In some embodiments, a carousel-type magazine reduces a longest dimension relative to a linear-type magazine, for a similar count of cartridges contained.

In an example of an operation cycle, dose puller 2314 is actuated to extend from the inhaler device into the carousel enclosure 2324, where it attaches to a dose cartridge 2300, for example, by means of latch mandibles 2302. In some embodiments, the dose puller 2314 "snaps" into place within the latch mandibles 2302. In some embodiments, the dose puller 2314 comprises two parts which move laterally past opposite sides of, and then close together within the space defined by the mandibles 2302 (potentially applying a lower force to the mandibles 2302 and/or cartridge 2300 than a snap-inserting method). A further action draws the actuator back into the inhaler device, and the attached cartridge 2300 along with it. The drug dose load 2304 of the cartridge 2300 is drawn thereby into communication with an air intake 2312. It is to be understood that a dose puller potentially operates in a mode other than transport by an actuated arm: for example as a dose "pusher" (comprising, for example a spring loaded member in the carousel volume itself), and/or a magnet (in a pulling mode) or magnets (in a pushing or pulling mode).

In some embodiments, clamping members 2310A and 2310B close on the cartridge, bringing electrodes into place for heating the drug dose for vaporization of the volatile substances within it.

Figures 11A, 11B, 11C:
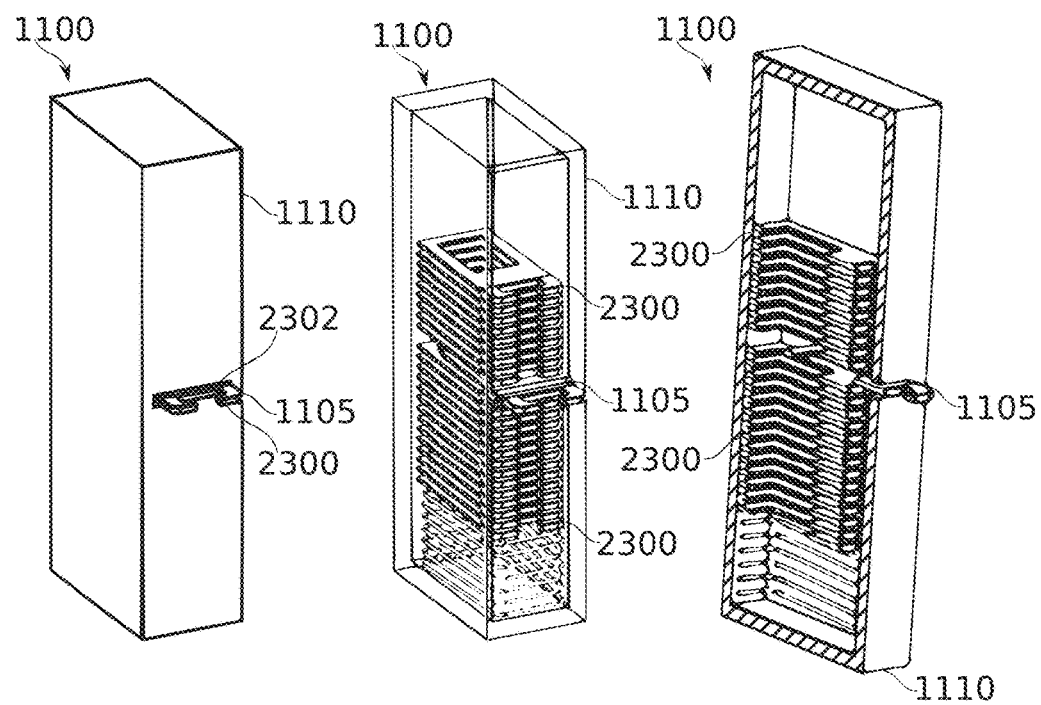
FIGS. 11A-11C schematically illustrate a linear-type dose cartridge magazine for use with an inhaler device, according to some embodiments.

Reference is now made to FIGS. 11A-11C, which schematically illustrate a linear-type dose cartridge magazine 1100 for use with an inhaler device, according to some embodiments. FIG. 11A shows an external view, the view of FIG. 11B shows magazine housing 1110 as partially transparent, and FIG. 11B shows the magazine 1100 in cross-section.

In some embodiments, a linear-type dose cartridge magazine 1100 comprises a housing 1110 having at least one cartridge access slot 1105, through which a dose cartridge 2300 is dispensed; for example, by gripping latch mandibles 2302 from a position at, protruding, or within access slot 1105. Optionally, the dose cartridges 2300 within the housing are transported by a spring, piston, screw, or other mechanism in one or both directions within the housing 1110. In some embodiments, cartridge transport is driven in whole or part by actions of withdrawing and/or replacing a cartridge. For example, in some embodiments, a cartridge 2300 is withdrawn from a first slot 1105, causing the next unused cartridge to be advanced into position for selection. In some embodiments, a cartridge 2300 is returned to a second slot (optionally, the same slot 1105, with an additional mechanism to control advancing), pushing a stack of used cartridges 2300 (e.g. a spring-loaded stack) deeper into a used-cartridge receptacle storage area. This provides a potential advantage for simplicity, security, and/or cost. In some embodiments, cartridges are optionally transported within housing 1110 under motorized control (for example, pushed by one or more plates in contact with a motorized lead screw). A potential advantage of motorized control is to allow non-sequential and/or non-predetermined access to dose cartridges—for example, to allow selection of a dose cartridge according to a pre-defined regimen, and/or a dynamically defined dose cartridge regimen.

Figure 7A:
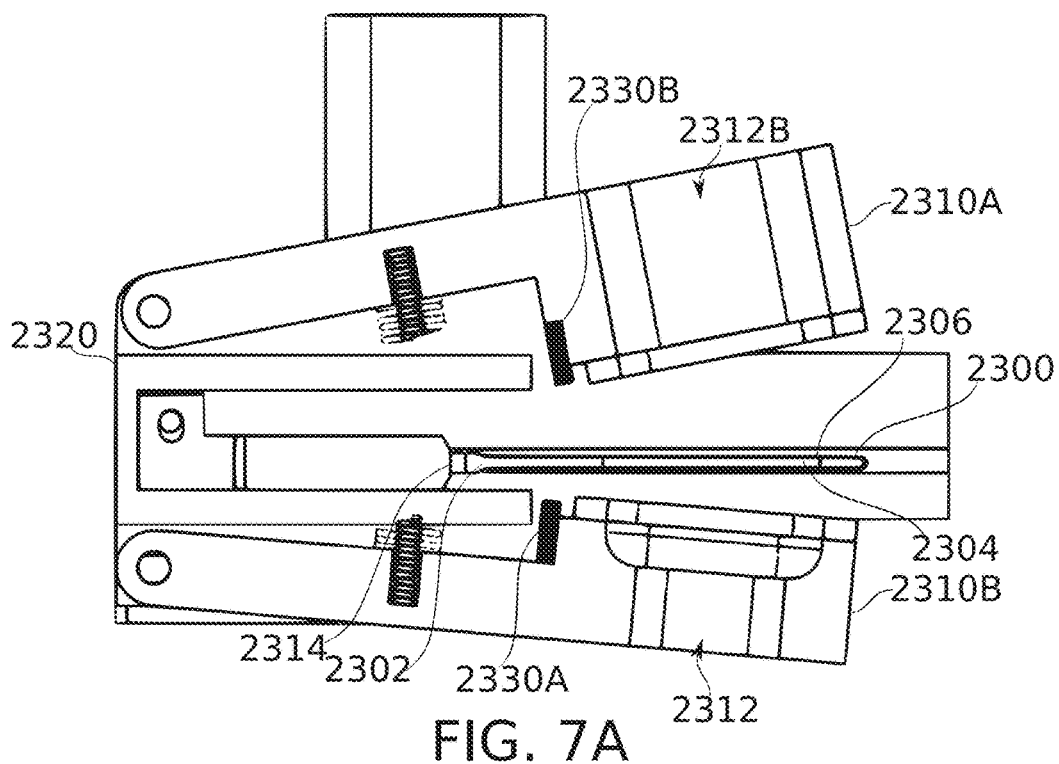
FIGS. 7A-7B schematically illustrate a clamping chamber for heating and delivery of vaporized substance from a dose cartridge, according to some embodiments.
Figure 7B:
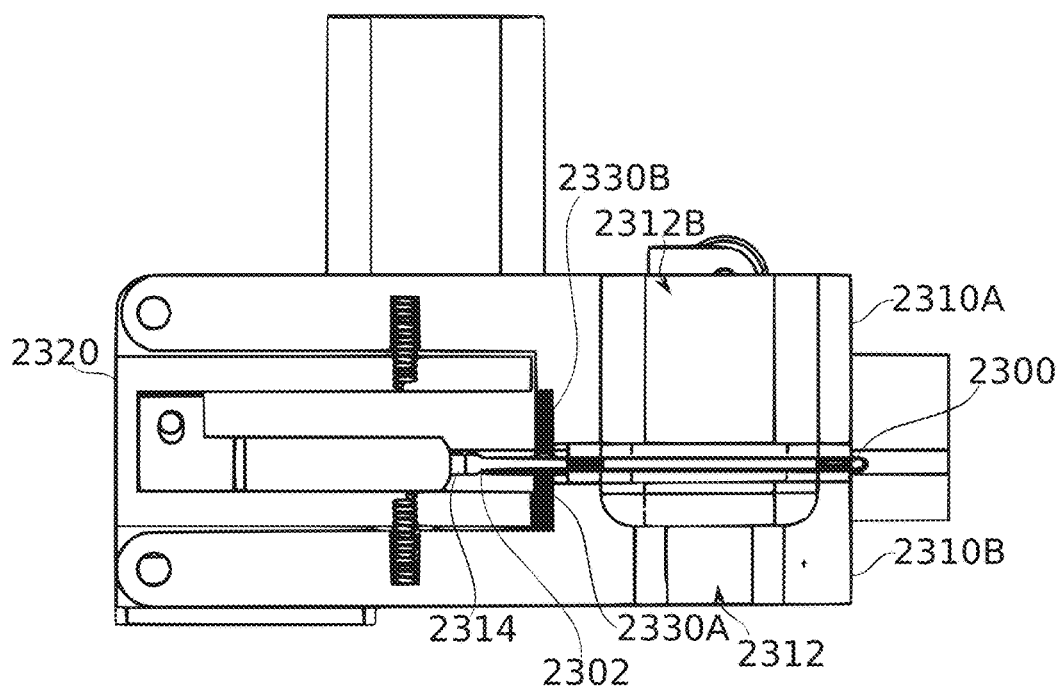
Figure 7C:
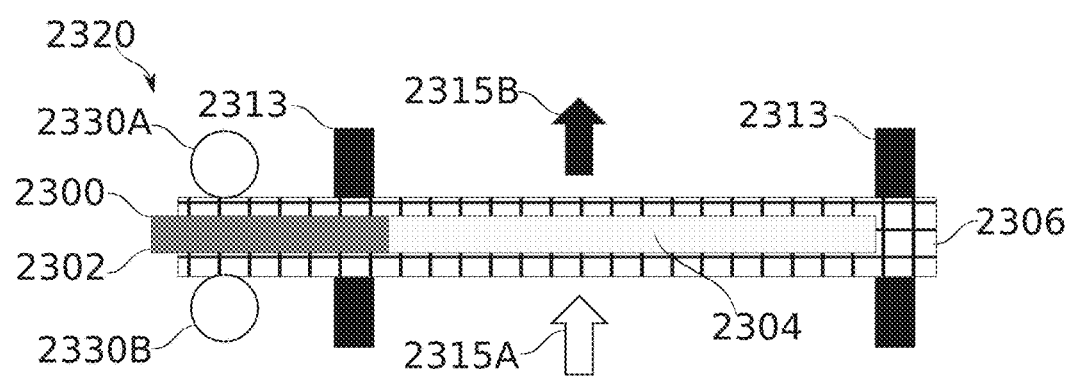
FIG. 7C schematically illustrates a cross section of a dose cartridge within a clamping chamber clamping a cartridge, according to some embodiments.

Reference is now made to FIGS. 7A-7B, which schematically illustrate a clamping chamber 2320 for heating and delivery of vaporized substance from a dose cartridge 2300, according to some embodiments. Reference is also made to FIG. 7C, which schematically illustrates a cross section of clamping chamber 2320 clamping a cartridge 2300, according to some embodiments.

In some embodiments, cartridge 2300 is transported into the clamping chamber 2320, for example by movement of dose puller 2314 while engaged with latch mandible 2302.

In some embodiments, clamping chamber 2320 comprises two clamping members 2310A, 2310B, which engage cartridge 2300 during dose vaporization. In some embodiments, each clamp 2310A, 2310B carries a corresponding electrode 2330A, 2330B, which is positioned to come into pressing contact with a resistive heating element 2306 or other heating element which the cartridge 2300 carries. Electrodes 2330A, 2330B are in turn in electrical contact with a power supply for supplying electrical current. Heating is delivered, in some embodiments, by switching current through the electrodes 2330A, 2330B, via the heating element 2306. Optionally, the electrodes 2330A, 2330B are positioned to contact the resistive heating element 2306 such that current follows pathways through the resistive heating element 2306 which extend over substantially all of at least one side (two sides, in the illustrated example) of the drug dose load, such that heat may be evenly distributed over and conducted to the surface of load 2304.

In some embodiments, air 2315A flow passes through intake 2312, through the heated drug dose load 2304, during which passage the air 2315A becomes drug substance laden air 2315B, and out of the output aperture 2312B. Optionally, the output aperture 2312B is in fluid communication with a tube which is routed for delivery of the vaporized substances to a user. Optionally, the clamping members 2310A, 2310B comprise portions of the intake 2312 and output 2312B. Potentially, this allows the clamp members 2310A, 2310B to alternately open for receiving a cartridge 2300, and close to seal an airway passage around the cartridge 2300, so that vaporized substance is kept confined to a defined passageway. In some embodiments, the clamp members 2310A, 2310B comprise air seals 2313, which close around the cartridge 2300 so as to substantially prevent substance vaporization and/or airflow transfer except along the pathway which conducts air to the user. Optionally, air seals 2313 comprise an elastically deformable material such as a polymer rubber. In some embodiments, electrodes 2330A, 2330B are also protected from the airflow by air seals 2313, optionally including any vaporizing portions of the pallet 2304. A potential advantage of closing the electrodes away from vaporized material is to reduces and/or prevent the electrodes from becoming contaminated due to repeated use.

In some embodiments, the electrodes 2330A, 2330B are block shaped (for example, as shown in FIGS. 7A-7B), providing a substantially planar contact surface with the heating element. In some embodiments, another electrode contact surface shape is used. In particular, a blade-like contact surface (long and thin, for example, with the thinner dimension being less than 0.5 mm, 0.3 mm, 0.1 mm, or another greater, smaller, or intermediate size), or a curved contact surface (for example, having an at least partially circular, elliptical, or other curved cross-section) is provided. Optionally, using such a shape reduces contact surface area, and concentrates clamping force, resulting in increased clamping pressure. This in turn potentially increases reproducibility of electrical contact and/or reduces electrical resistance (and energy losses) at the region of electrical contact with the cartridge. For example, the inventors have found that, in some embodiments, an electrode/heating element contact force of about 500 N, used with a curved contact surface electrode design (and/or, for example, a pressure of about 70 N/mm$^2$), reduces electrical contact resistance to substantially zero (for example, less than 1% of total circuit resistance). In some embodiments, power loss due to resistance across the electrical contact is less than, for example, about 1%. In particular, a curved (for example, cylindrical) electrode contact surface provides a potential advantage for reproducible contact by combining a low contact surface with robust mechanical support behind the surface.

After dose delivery, ejection of the cartridge comprises disengagement of dose puller 2314 from latch mandible 2302; for example, by displacing one of the two parts while restraining the other from following, and/or by deforming one of the two parts. For example, puller 2314 is further retracted, while cartridge 2300 is prevented from following by a restriction in the size of the slot through which it moves. In some embodiments, disengagement is followed by ejection: for example, the cartridge falls out of its slot, is pushed by a returning action of the dose puller 2314, and/or is otherwise transported out of the device altogether. In some embodiments, the cartridge is returned to carousel 2322 as a used dose (into the same, or another available slot different from the one it was retrieved from). Optionally, this is performed shortly or immediately at the end of use. Alternatively, the cartridge is ejected in the framework of a next use of the device, in which case the carousel also advances to present the next cartridge to be used.

In some embodiments, access to doses loaded in the carousel is sequentially in the order of their positions within the carousel. In some embodiments, dosage order is predetermined but variable; for example, dosages of different amounts for administration throughout a period of time are arranged in that order when the carousel is loaded. In some embodiments, carousel movement (advancing) is substantially according to a sequence of actions which are mechanically coupled to the dose pulling and/or dose returning actions. In some embodiments, carousel movement (or dose cartridge selection for another magazine type, such as a linear-type magazine) is under the control of a controller, for example, a microprocessor-controlled stepper motor or other advancing mechanism. Optionally, the controller tracks which dosage is in which cartridge slot, and/or its status. Optionally, the controller automatically and/or upon command selects an appropriate cartridge, and advances it into use position by as many steps as needed to make it available for pulling. Optionally, this selection allows out-of-order access to cartridges in the carousel (or other magazine configuration). Optionally the carousel or other magazine advances as a result of a user actuating the device. In some embodiments, there is more than one use position (for example, there are two or more clamping chambers) and the controller is configured to select a combination of cartridges from the magazine from any specified location within the magazine. In some embodiments, a controller selects a dose according to a progress of a dosing regimen. For example, if a first drug dose is determined to have been only partially administered (for example, due to a detected problem during inhalation), the controller optionally selects a second partial dose, for additional administration. Additionally or alternatively, the strength of a drug dose is selected by a controller based on a time elapsed since a previous dose was administered. This potentially allows repeated dosing by a user, while maintaining control which potentially prevents overdosing.

In some embodiments, a controller is configured to present dose cartridges 2300 from a magazine or other cartridge holder for a plurality of inhalations to be taken sequentially as part of a single dosing, for example in a single session, or a plurality of sessions separate by brief intervals. Optionally, the device advises the user before the use on the number of inhalations to be performed and the user simply takes the number of inhalations with the device as instructed, while the device automatically selects the cartridges in accordance with a certain regimen. In some embodiments, the user is prompted (for example, by an audible or visible stimulus) as long as there are additional doses remaining in the current inhalation series. Optionally, the controller replaces dose cartridges automatically as they are used. Alternatively, the user is prompted to perform an action for dose cartridge replacement (for example, moving the mouthpiece or pressing a button). Optionally, the device is configured to enforce a minimum interval between inhalations. This is a potential advantage to reduce the likelihood that a user will perform one or more of the later inhalations improperly. For example, a minimal time period of about 2-5 minutes is optionally imposed by the device between each inhalation and/or dose exchange. Additionally or alternatively, a rapid sequence of inhalations (e.g. separated by no more than a few seconds) is performed as fast as is convenient to the user (i.e. without an imposed minimal interval). This provides the potential advantage of being less time consuming in total. Optionally, one or more minimal interval periods are imposed when a sequence of inhalations is long enough to warrant a mandatory rest of the user and prevent shortness of breath.

Detachable Vaporizing Device

Figure 8A:
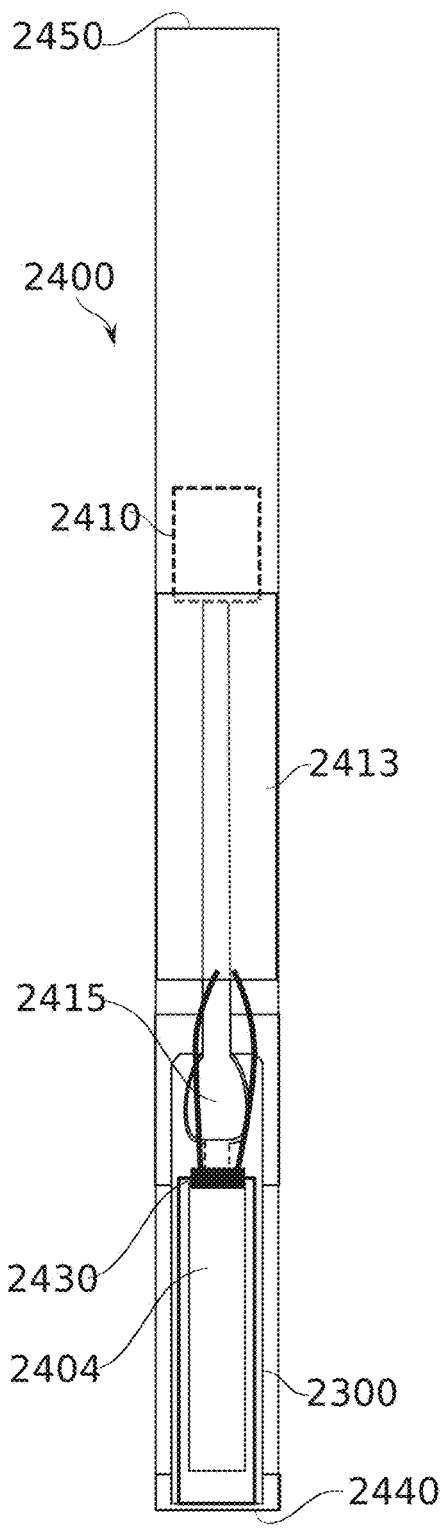
FIGS. 8A-8B schematically illustrate a dose delivery device for loading from a dose magazine (e.g. a carousel), and separable from the magazine for delivery of the dose itself, according to some embodiments.
Figure 8B:
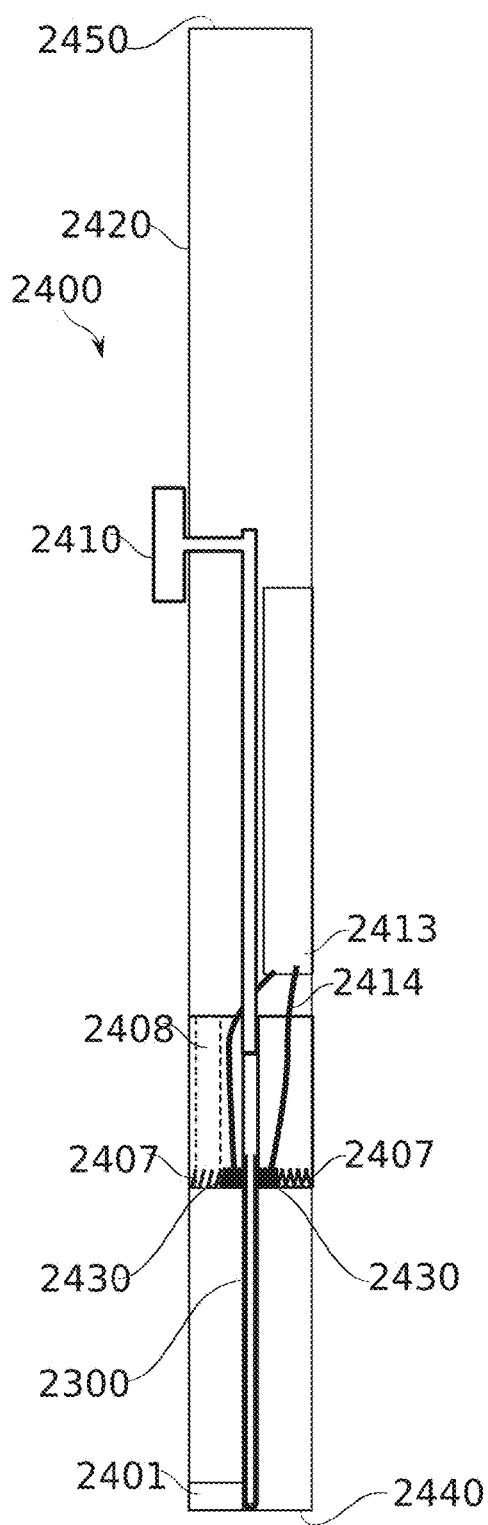

Reference is now made to FIGS. 8A-8B, which schematically illustrate a dosage delivery device for loading from a carousel, and separable from the carousel for delivery of the dose itself, according to some embodiments.

In some embodiments, functions performed by clamping chamber assembly 2320 are performed by separable parts, such that a clamping/heating/administration subassembly is separable from portions of a dose storage pulling and transport subassembly, at least for dose administration to a user. In some embodiments, the clamping/heating/administration assembly 2400 comprises a substantially cylindrical body (for example, cigarette, cigarillo, cigar, and/or pen shaped), which inserts into a receptacle of the dose pulling and transport assembly. The assembly 2400 comprises a slider mechanism 2410 or other structure which is engaged by the transport assembly, and/or is activated by manual or other external operation.

Optionally, slider mechanism 2410 slides out of the intake end 2440 of the assembly 2400 to engage a cartridge 2300 with engaging part 2415, as described, for example, in relation to dose puller 2314. Optionally, the cartridge 2300 (formed, for example, with a long and narrow drug dose load 2404) is pulled into the clamping/heating assembly. The clamping/heating assembly optionally comprises electrodes 2430 which are loaded with spring members 2407, or another means, for pressing against resistive heating element 2306 to provide electrical contact thereto. Optionally, power for heating is supplied by a battery 2413 connected to electrodes 2430 via wires 2414. Optionally, the battery 2413 is rechargeable, for example, the battery 2413 recharges from a supply provided by the main body assembled together with the carousel. Optionally, heating begins upon operation of a control (such as a button), and/or is subject to one or more automatic activation, modulation, and/or interlock controls, such as heating upon sensing of a change in pressure, and/or air shunt opening to control speed and/or amount of dose delivery. During dose delivery, air is drawn through the body 2420 (for example, orally), by applying suction to end 2450. Air drawn into intake end 2440 is forced by baffles/conduits 2401, 2408 to pass through the heated drug dose load 2404, carrying vaporized drug substance to end 2450.

A potential advantage of the separable design is to reduce the effort required by a user to manage the dosing device at the time of dose administration. Another potential advantage is to separate the functions of dosage selection, management, and control from the dosing itself. There is a potential positive psychological effect due the separation of the dosing act, which approximates that of a normal e-cigarette, from the more clinical aspects of dosage control.

In some embodiments, a removable cartridge comprises a plurality of separately heatable regions; for example, material is loaded into different apertures, and/or an aperture which is crossed by a plurality of separately addressable heating elements. Optionally, the different loads comprise different substances. For example, a *cannabis* load is optionally followed by one or more tobacco loads, and/or by loads of *cannabis* that have a different, or even no, THC content.

In some embodiments, analog and/or digital circuit logic is used to control which heating element region receives current. For example, each heating element is optionally deliberately "burned" (by fuse breaking, for example) after use. A suitably arranged sensing circuit detects a first unused dosing region, and selects it for the next activation. A potential advantage of this is to allow a dosage to be spread over multiple inhalations. Another potential advantage is to allow a dosage for one purpose (for example, a medicinal purpose) to be combined with dosages for another purpose (for example, an alternative medicinal purpose, or to allow additional inhalations for the purpose of enjoyment). Another potential advantage is to allow the use of multiple dose types (for example, different flavors) for the sake of giving variety to the user's experience.

Figure 9:
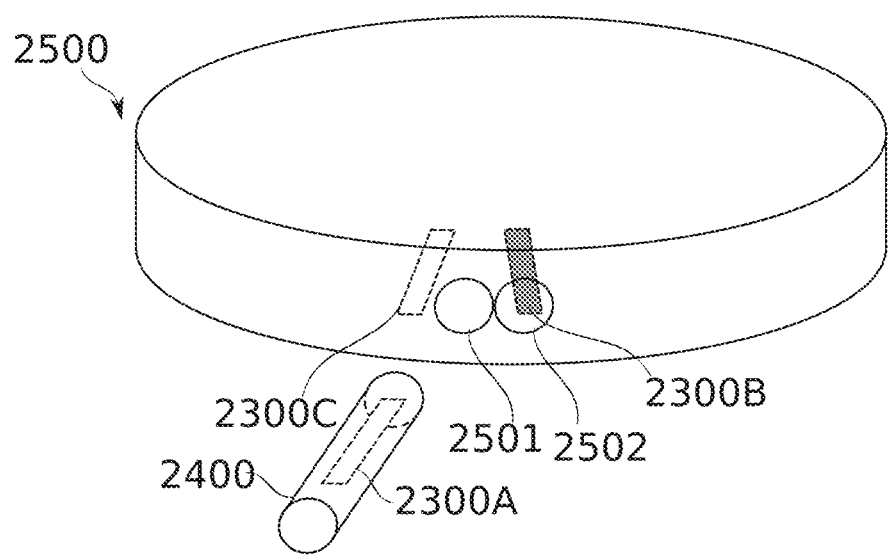
FIG. 9 schematically illustrates an interlock-protected dose dispensing device, together with a removable dose administration assembly, according to some embodiments.

Reference is now made to FIG. 9, which schematically illustrates an interlock-protected dose dispensing device 2500, together with a removable dose administration assembly 2400, according to some embodiments.

In some embodiments, dispensing device 2500 comprises a plurality of receiving apertures 2501, 2502 for the administration assembly 2400. In some embodiments, aperture 2501 is an aperture from which an unused dose cartridge 2300C, 2300A is retrieved into administration assembly 2400. In some embodiments, after a dose cartridge 2300A is extracted from the dispensing device 2500, the next dose cartridge 2300C does not advance into position until the conditions enforced by an interlock device are met. In some embodiments, operation of the interlock device comprises inserting administration assembly 2500 into aperture 2502. Optionally, insertion triggers (for example, by mechanical and/or controller-actuated operation) the movement of the carousel such that a dose cartridge 2300C is moved into position. In some embodiments, insertion (optionally insertion and removal) of the administration assembly 2400 extracts cartridge 2300A, which now occupies the former position of used cartridge 2300B. Potentially, this interlock mechanism helps to ensure that only one dose at a time is removed from the dispensing device 2500. In some embodiment, advancing of the carousel does not occur unless a cartridge 2300A is sensed within the administration assembly 2400 upon insertion into aperture 2502. In some embodiments, cartridge 2300A is inserted into administration assembly 2400 such that it cannot be removed without destruction of the cartridge 2300A and/or the administration assembly 2400.

Plurality of Potentially Simultaneous Doses

Figure 10:
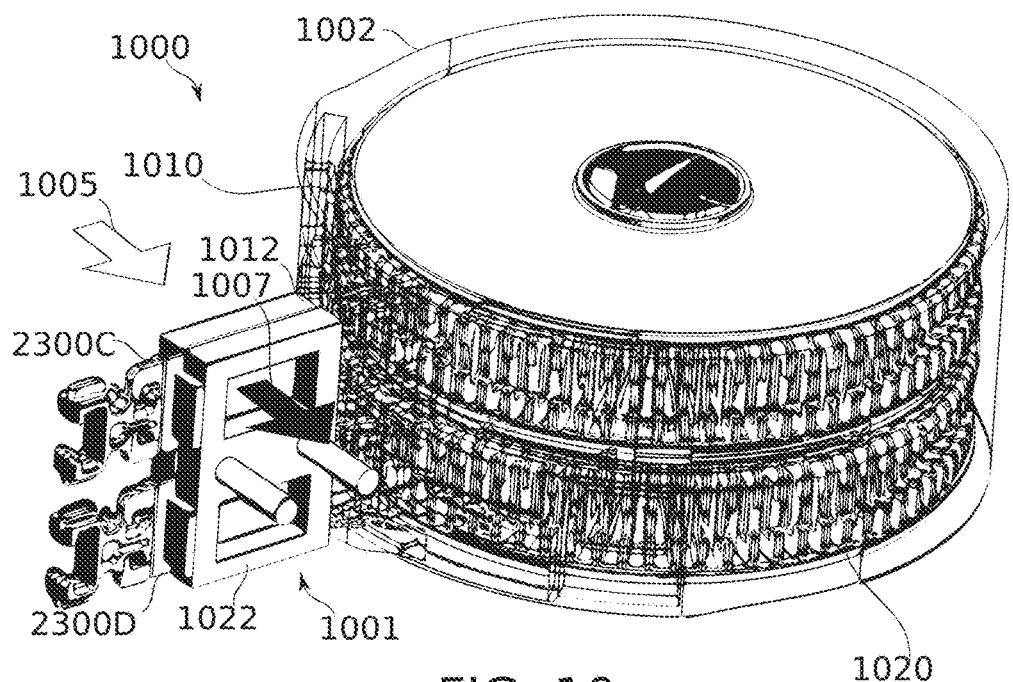
FIG. 10 schematically illustrates a carousel arranged for potentially simultaneous administration of substances from a plurality of dose cartridges held within two separate carousel magazines, according to some embodiments.

Reference is now made to FIG. 10, which schematically illustrates a carousel arranged for potentially simultaneous administration of substances from a plurality of dose cartridges held within two separate carousel magazines, according to some embodiments.

In some embodiments, a dispensing device 1000 comprises a plurality of magazines, shown here as carousel magazines 1010, 1020; each operating, for example, as described in relation to the carousel of FIGS. 6A-6E. In some embodiments, the magazines 1010, 1020 are stacked, and the cartridge holding chambers 1012, 1022 are arranged to share a common conduit, or two at least partially parallel conduits for extraction airflow. Magazines 1010, 1020 are optionally housed in a common housing 1002 (shown transparent to reveal interior details), or provided with separate housings.

In some embodiments, operation of the device comprises removal of a first dose cartridge 2300C from the first magazine 1010, and a second dose cartridge 2300D from the second magazine 1020. The dose cartridges are positioned one adjacent the other in a shared clamping chamber 1001 (optionally, two separately actuatable clamping chambers are provided). Unladen air 1005 flows via the dose cartridges 2300C, 2300D; laden air 1007 exits them bearing at least one drug substance. The applied heating profile (comprising time, temperature, heating rate and/or onset, for example) is optionally identical in the two dose cartridges. Optionally, the applied heating profiles are controlled separately, thus optionally releasing the drug substance(s) at different times, and/or releasing different drug substance compositions and/or amounts).

Optionally, airflow is estimated and controlled for both dose cartridges 2300C, 2300D in unison. Optionally, only one dose cartridge comprises a drug substance, and a second, inert cartridge occupies the other dose cartridge position. An inert cartridge is, for example, a cartridge that does not comprise a substance (e.g., comprises an inert pallet).

Optionally an inert cartridge has similar airflow properties to those of a dose cartridge it is used with. As an alternative option, the inert cartridge entirely blocks airflow. Optionally, a used cartridge is used as an inert cartridge.

In some embodiments, the inert cartridge is included in a normal position of the magazine. Optionally, the inert cartridge is stored in the device at another accessible location. Optionally the empty position is blocked, for example by a protrusion from a wall.

In some embodiments, an inert cartridge (for example, a blocker cartridge or partition) is present in the dose cartridge magazine positions by default (for example, placed during manufacture of the magazine, before drug loading). When moving a dose cartridge into position during drug loading, the inert cartridge is optionally removed and replaced by the dose cartridge as part of loading. Where no dose cartridge is loaded, the partition optionally remains. Once a used dose cartridge is discarded, the inert cartridge optionally returns to position, for example by a spring mechanism.

Figure 12:
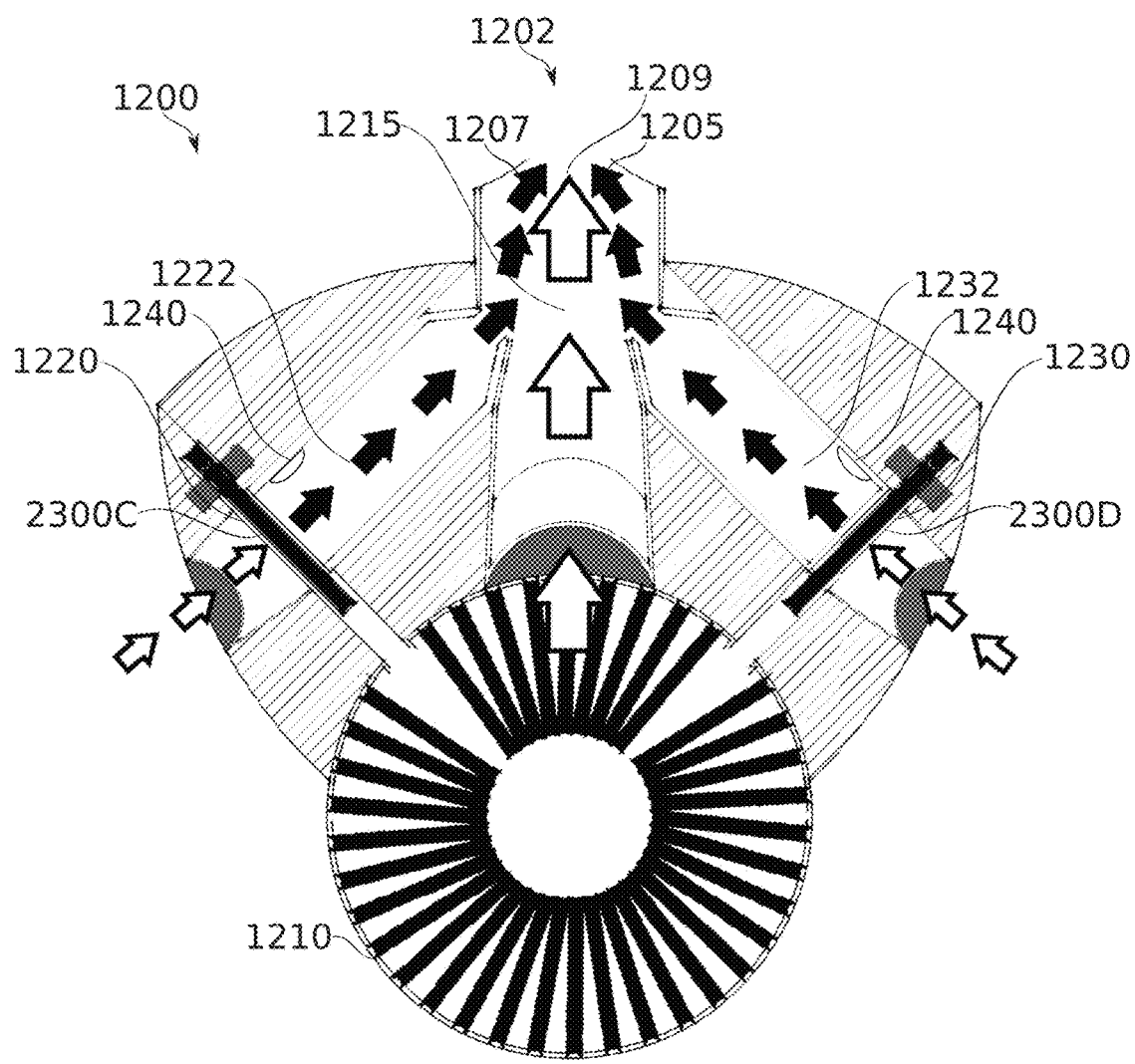
FIG. 12 schematically illustrates a carousel arranged in an inhaler for simultaneous administration of substances from a plurality of dose cartridge clamping chambers in a corresponding plurality of extraction airflow conduits, according to some embodiments.

Reference is now made to FIG. 12, which schematically illustrates a carousel 1210 arranged in an inhaler 1200 for simultaneous administration of substances from a plurality of dose cartridge clamping chambers 1220, 1230 in a corresponding plurality of extraction airflow conduits 1222, 1232, according to some embodiments.

In some embodiments, a plurality of separate extraction airflow conduits 1222, 1232 are provided, each comprising a dose cartridge clamping chamber 1220, 1230. Optionally, dose cartridges 2300C, 2300D are drawn from a single carousel magazine 1210 or other cartridge magazine. Alternatively, a plurality of magazines is provided. Cartridge drawing is optionally simultaneous, sequential and/or separately operated altogether, and optionally while the cartridge magazine(s) remain in a single position, or with movement of the magazine 1210 (e.g. rotation) between draws.

In some embodiments, flow through the extraction conduits 1222, 1232 is at least partially regulated by providing a draw conduit 1215 in flow communication with the extraction conduits 1222, 1232. The total flow of air 1209 through the device due to inhalation from a mouthpiece 1202 is optionally divided among all conduits (for example by the sizing and/or size adjustment of conduit diameters and/or valves), such that the portion of airflow through each extraction conduit 1222, 1232 is adjusted to be within a targeted extraction airflow profile. Remaining airflow is optionally directed through the draw conduit 1215. Optionally, the extraction conduits are operated separately (for example, only one is operated, or both are operated in sequence).

Optionally, sensors 1240 providing data (e.g. airflow and/or temperature data indicative of airflow and/or temperature at the dose cartridges during operation) for control are optionally positioned near or via one or more of the dose cartridges 2300C, 2300D. Control optionally comprises adjustment of airflow (for example, by adjustment of a valve or aperture position) such that both dose cartridges 2300C, 2300D simultaneously experience airflow 1205, 1207 within a given range. Alternatively, adjustment is such that a part of the airflow sequence is controlled with respect to a first dose cartridge position 1220, while another part is controlled according to second position 1230. Optionally, in some sessions, only one of clamping chambers 1220, 1230 is used.

In some embodiments, a plurality of draw conduits 1215 is provided, for example, one in separate association with each of the extraction conduits 1222, 1232. Optionally, the air flowing in each of the extraction conduits 1222, 1232 is combined only at the mouthpiece. A potential advantage of this is to allow separate control of airflow through each dose cartridge.

In some embodiments, a third type of conduit (not shown, but described as a "general conduit" in, for example, a co-filed application designated "Flow Regulating Inhaler Device", referenced hereinabove) comprises a valved conduit with a low airflow resistance when valved open. Optionally, a conduit of this third type is opened for admission of ambient air during inhalation, for example to provide an advancing (or "chase") airflow behind airflow laden with a drug substance. This is a potential advantage for moving drug substance laden air past a respiratory dead space, and/or into a deeper portion of the lungs for absorption.

Reference is now made to FIGS. 13A-13B, which schematically illustrate a linear-type cartridge magazine 1302 and dual-dose cartridge transport 1300 in two sequential positions, according to some embodiments. Reference is also made to FIGS. 13C-13D, which schematically illustrate the dual-dose cartridge transport 1300 of FIGS. 13A-13B in two sequential positions, according to some embodiments.

In each of FIGS. 13A and 13C, two pullers 2314 are shown engaged with two dose cartridges 2300C, 2300D, preparatory to pulling the dose cartridges 2300C, 2300D into position for substance vaporization. In each of FIGS. 13B and 13D, the cartridges 2300C, 2300D are shown in position for vaporization.

In some embodiments, an inhaler device includes a clamping chamber 1300 configured to clamp two or more dose cartridges 2300C, 2300D along an airflow conduit through which air flows to extract one or more drug substances from the dose cartridges 2300C, 2300D. Arrows 1305, 1307 respectively and schematically represent airflow unladen with drug substance into the dose cartridges, and airflow laden with drug flow out of the dose cartridges.

In some embodiments, clamping chamber 1300 comprises two dose pullers 2314 and associated dose cartridge transport mechanisms. The dose pullers 2314 are positioned to pull a dose cartridge into the cartridge transport where they are positioned in sequence along an airflow conduit. Optionally, a clamping mechanism (not shown for clarity) is also provided; the functions of the clamping mechanism include, for example, electrode positioning and sealing of the airflow conduit.

In some embodiments, loading and/or heating of the dose cartridges is separately actuatable. Optionally, one or both dose cartridges 2300C, 2300D are positioned in the clamping chamber for use. Optionally, both are positioned, but only one is heated, the two are heated at different times, and/or the cartridges 2300C, 2300D are subjected to different heating profiles (comprising time, temperature, heating rate and/or onset, for example).

Optionally, a plurality of dose cartridges 2300C, 2300D comprise a single dose for a given inhalation. Optionally, airflow is estimated and controlled for the plurality of dose cartridges 2300C, 2300D in unison, essentially as described with respect to single dose cartridge clamping chamber embodiments herein.

It is noted that the temperature of air reaching a second dose cartridge along the path is potentially higher than ambient temperature due to passage through a first heated dose cartridge. Optionally, this is taken into account when setting a heating profile for the dose cartridges. In some embodiments the dose cartridges are heated in sequence with downstream doses heating before upstream ones.

Optionally, dose pullers 2314 are actuated together for dose cartridge transport. Alternatively, each puller 2314 is actuated separately to pull a specific dose cartridge from a specific location in the magazine. For example, a first dose cartridge 2300C is taken by a first puller 2314 and then the dose cartridges are shifted in the magazine such that another dose cartridge 2300D is available at a position accessible by the second puller 2314. Optionally, the first dose cartridge 2300C is taken when the user presses a button, positions the mouthpiece for use, or otherwise actuates the inhaler for dose cartridge transport. Optionally, the second dose cartridge 2300D is taken automatically by the controller, or also taken up in response to the same or a second actuation by the user.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A dose cartridge for an inhaler device, the dose cartridge comprising:
   a flat pallet of airflow-permeable material including a heat-vaporizing drug substance, the pallet having two opposing faces and being positioned in the dose cartridge so as to expose the two faces to airflow;
   a supporting member coupled to the pallet to support the pallet from at least one side of the pallet joining the two faces; and
   an electrically resistive heating element extending at least partially across at least one of the two opposing faces from an attachment with the supporting member;
   wherein the resistive heating element is in thermal contact with and extends across at least two opposite surfaces of the pallet and comprises a U-shape with two ends around a hollow in which the pallet is positioned.

2. The inhaler dose cartridge of claim 1, wherein an electrical current flows across the two opposite surfaces when a voltage is applied between said two ends.

3. The inhaler dose cartridge of claim 1, wherein at least a portion of the resistive heating element extending across the pallet is permeable to the passage of air.

4. The inhaler dose cartridge of claim 1, wherein a portion of the resistive heating element extending across the pallet comprises a barrier which prevents a granulate portion of the pallet from leaving the inhaler dose cartridge.

5. The inhaler dose cartridge of claim 4, wherein at least a portion of the resistive heating element is embedded in the supporting member.

6. The inhaler dose cartridge of claim 1, wherein the resistive heating unit comprises a woven mesh.

7. The inhaler dose cartridge of claim 1, wherein the resistive heating unit comprises at least one ribbon of etched metal foil.

8. The inhaler dose cartridge of claim 1, wherein said material comprises *cannabis*.

9. The inhaler dose cartridge of claim 1, wherein said material comprises tobacco.

10. The inhaler dose cartridge of claim 1, comprising a plurality of heating element regions, each region being separately configured to receive electric current.

11. The inhaler dose cartridge of claim 10, wherein the plurality of heating elements is associated with a corresponding plurality of pallets.

12. The inhaler dose cartridge of claim 1, wherein the supporting member comprises a geometry shaped for attachment to the transport arm of a dose puller.

13. The inhaler dose cartridge of claim 1, wherein at least a portion of said dose cartridge is configured to allow a flow through said pallet at a rate of at least 0.5 liters of gas per minute under a pulling vacuum of at least 1 kPa.

14. The inhaler dose cartridge of claim 1, wherein the supporting member comprises a hollow region open on at least one of the two faces, said hollow region shaped and sized to contain said pallet.

15. The inhaler dose cartridge of claim 1, wherein the resistive heating element is a metal resistive heating element.

16. A dose cartridge for an inhaler device, the dose cartridge comprising:
  a flat pallet of airflow-permeable material including a heat-vaporizing drug substance, the pallet having two opposing faces and being positioned in the dose cartridge so as to allow air to flow in through one of said faces, through said pallet, and out the other face;
  a supporting member coupled to the pallet to support the pallet from at least one side of the pallet joining the two faces; and
  an electrically resistive heating element extending at least partially across at least one of the two opposing faces from an attachment with the supporting member;
  wherein a portion of the resistive heating element extending across the pallet comprises a barrier which prevents a granulate portion of the pallet from leaving the inhaler dose cartridge; and
  wherein the supporting member comprises a geometry shaped for attachment to a transport arm of a dose puller.

17. The inhaler dose cartridge of claim 16, wherein at least a portion of the resistive heating element extending across the pallet is permeable to the passage of air.

18. The inhaler dose cartridge of claim 16, wherein the resistive heating unit comprises at least one ribbon of etched metal foil.

19. The inhaler dose cartridge of claim 16, wherein at least a portion of the resistive heating element is embedded in the supporting member.

20. The inhaler dose cartridge of claim 16, wherein said material comprises *Cannabis*.

21. The inhaler dose cartridge of claim 16, wherein said material comprises tobacco.

22. The inhaler dose cartridge of claim 16, comprising a plurality of heating element regions, each region being separately configured to receive electric current.

23. The inhaler dose cartridge of claim 16, wherein the supporting member comprises a hollow region open on at least one of the two faces; said hollow region shaped and sized to contain said pallet.

24. The inhaler dose cartridge of claim 16, wherein said pallet comprises granulate that is compressed to a degree of density that allows for the passage of said flow of air through said granulate.

25. The inhaler dose cartridge of claim 1, wherein said supporting member includes said resistive heating element.

* * * * *

UNITED STATES PATENT AND TRADEMARK OFFICE
CERTIFICATE OF CORRECTION

Page 1 of 1

PATENT NO. : 10,099,020 B2
APPLICATION NO. : 15/308370
DATED : October 16, 2018
INVENTOR(S) : Perry Davidson et al.

It is certified that error appears in the above-identified patent and that said Letters Patent is hereby corrected as shown below:

On the Title Page

In item (72) Inventors:
After "Roee Lifshitz, Moshav Beit Hillel (IL)",

Insert the following:
-- Shay Landa, Tel-Aviv (IL) --

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*